(12) United States Patent
Drasler et al.

(10) Patent No.: US 6,241,763 B1
(45) Date of Patent: Jun. 5, 2001

(54) IN SITU VENOUS VALVE DEVICE AND METHOD OF FORMATION

(76) Inventors: William J. Drasler, 4100 Dynasty Dr., Minnetonka, MN (US) 55345; Joseph M. Thielen, 3027 Cameron Ave. SE., Buffalo, MN (US) 55313

( * ) Notice: Subject to any disclaimer, the term of this patent is extended or adjusted under 35 U.S.C. 154(b) by 0 days.

(21) Appl. No.: 09/328,835

(22) Filed: Jun. 8, 1999

(51) Int. Cl.[7] ........................................................ A61F 2/06
(52) U.S. Cl. ............................................................ 623/1.24
(58) Field of Search ................................. 623/1.24–1.27, 623/1.41, 2.12, 2.13, 2.15, 2.16

(56) References Cited

U.S. PATENT DOCUMENTS

| | | |
|---|---|---|
| 4,904,254 | 2/1990 | Lane . |
| 5,147,389 | 9/1992 | Lane . |
| 5,358,518 | 10/1994 | Camilli . |
| 5,476,471 | 12/1995 | Shifrin . |
| 5,500,014 | 3/1996 | Quijano . |
| 5,810,847 | 9/1998 | Laufer . |

FOREIGN PATENT DOCUMENTS 0 856 300 A1  * 8/1998 (EP) ............................ 623/FOR 100

* cited by examiner

Primary Examiner—David H. Willse

(57) ABSTRACT

A venous valve device and method of formation are described to provide antegrade blood flow in the deep venous vessels of the leg or in other venous vessels of the body having incompetent or irreversibly dysfunctional valves. A venous valve is formed in situ from autologous vein conduit not having a valve present locally. An overlap region is formed by attaching two opposing walls of the vein together in a generally axial direction forming two tubular regions. One region provides antegrade blood flow and the other region provides a sinus cavity that is filled during the initiation of retrograde blood flow. A valve cusp is formed by attaching vessel wall together forming a commissure that extends between the two overlap regions. A single valve cusp moves toward the sinus cavity to allow antegrade blood flow and moves away from the sinus cavity to block retrograde blood flow. Inlet and outlet transition regions can be formed to provide hemodynamic antegrade blood flow through the valve. The autologous tissue valve remains endothelialized to prevent thrombus deposit in the valve. The venous valve can also be formed from biological tissue from an autologous, heterologous, or other tissue source and implanted interpositionally at the site of valvular incompetency.

42 Claims, 40 Drawing Sheets

IN SITU VENOUS VALVE DEVICE AND METHOD OF FORMATION

BACKGROUND OF THE INVENTION

1. Field of Invention

The present invention relates to a device and method for a vascular valve for the vascular system and more specifically for the venous vascular system of the human body and a method for forming the venous valve and more specifically for forming the venous valve from a native vein that may have been enlarged diametrically within the patient causing the naturally occurring venous valve to become incompetant.

2. Description of Prior Art

Venous valves are found within native venous vessels and are used to assist in returning blood back to the heart in an antegrade direction from all parts of the body. The venous system of the leg for example includes the deep venous system and the superficial venous system, both of which are provided with venous valves which are intended to direct blood toward the heart and prevent backflow or retrograde flow which can lead to blood pooling or stasis in the leg. Incompetent valves can also lead to reflux of blood from the deep venous system to the superficial venous system and the formation of vericose veins. Superficial veins which include the greater and lesser saphenous veins have perforating branches in the femoral and popliteal regions of the leg that direct blood flow toward the deep venous system and generally have a venous valve located near the junction with the deep system. Deep veins of the leg include the anterior and posterior tibial veins, popliteal veins, and femoral veins. Deep veins are surrounded in part by musculature tissue that assist in generating flow due to muscle contraction during normal walking or exercising. Veins in the lower leg have a static pressure while standing of approximately 80–90 mm Hg and this pressure can be reduced during exercise to 60–70 mm Hg. Despite exposure to such pressures, the valves of the leg are very flexible and can close with a pressure drop of less than one mm Hg. Due to the endothelial covering on the venous valves, they are able to remain patent and resist thrombosis with blood flow rates of less than 50 ml/min found typically in some of the smaller veins of the lower leg. Although the present invention has direct application to the treatment of venous valvular dysfunction of the leg, it is understood that the invention is not limited to this application and can be applied equally well to the treatment of veins throughout the human body as well as other tubular elements of the body requiring a valve.

Veins typically in the leg can become distended from prolonged exposure to excessive pressure and due to weaknesses found in the vessel wall causing the natural venous valves to become incompetent leading to retrograde blood flow in the veins. Such veins no longer finction to help pump or direct the blood back to the heart during normal walking or use of the leg muscles. As a result, blood tends to pool in the lower leg and can lead to leg swelling and the formation of deep venous thrombosis and phlebitis. The formation of thrombus in the veins can further impair venous valvular function by causing valvular adherence to the venous wall with possible irreversible loss of venous function. Continued exposure of the venous system to blood pooling and swelling of the surrounding tissue can lead to post phlebitic syndrome with a propensity for open sores, infection, leading to possible limb amputation.

Repair and replacement of venous valves presents a formidable problem due to the low blood flow rate found in native veins, the very thin wall structure of the venous wall and the venous valve, and the ease and frequency of which venous blood flow can be impeded or totally blocked for a period of time. Surgical reconstruction techniques used to address venous valve incompetence involve venous valve bypass using a segment of vein with a competent valve, venous transposition to bypass venous blood flow through a neighboring competent valve, and valvuloplasty to repair the valve cusps. These surgical approaches are described in medical journals and in standard surgical text books. These surgical techniques are highly technique dependent and difficult to perform by a highly trained vascular surgeon.

The presence of a low or intermittent blood flow rates found in the veins of the lower leg requires that any suitable venous valve replacement contain an endothelial covering to protect the vessel against thrombosis. Blood stoppage for a period of time in contact with most foreign material can result in thrombus formation, and ensuing failure of any venous valve constructed of a polymeric material or some biomaterials.

Quijano describes in U.S. Pat. No. 5,500,014 the use of a biological valvular prosthesis that is obtained from the jugular vein of an animal. The valve is chemically fixed to give it strength. The fixing process tends to cause such valves to be stiff and calcification has been known to occur at flexation sites. Another problem with valves of this type is their lack of forming a stable endothelium with the resulting formation of thrombus when blood flow is impeded or temporarily blocked. Others have tried constructing venous valves out of a biological tissue material obtained from another species or the same species. Some tissues that have been used include pericardium and venous tissue treated with a crosslinking treatment. These devices have suffered problems associated with calcification, tissue degradation, tissue rejection, acute thrombosis, long term thrombosis, and valvular failure due to mechanical dysfunction.

Another vascular prosthesis that is constructed out of polymeric or metallic components is described by Camilli is U.S. Pat. No. 5,358,518. He describes a movable rigid or semi-rigid plate that pivots and allows unidirectional blood flow through the venous tube. The biomaterials used in the device of Camilli will not form a stable endothelium on the blood flow surface; due to the low blood flow and often times interrupted blood flow found within the venous system, this device will be prone to thrombosis and failure.

Laufer (U.S. Pat. No. 5,810,847) describes an appliance that is constructed out of a biomaterial that is attached to the cusps of an existing venous valve. Such a polymeric appliance will have a propensity to thrombosis in the low blood flow conditions found in the venous system. Also, many patients with venous problems do not have suitable valves onto which the appliance described by Laufer can be attached.

Lane describes in U.S. Pat. Nos. 5,147,389 and 4,904,254 and Shifrin describes in U.S. Pat. No. 5,476,471 devices that are intended to surround the outer surface of incompetent or insufficient venous valves. These devices are intended to reduce the diameter of the vessel in the region of the incompetent valve allowing the natural cusps to approximate each other leaving the valve commissures intact. For these devices to work properly, the valves of the vein must not be adherent to the vessel wall, this adherent condition is often found when the vessel is exposed to deep venous thrombosis. This significantly limits the patient population that can benefit from a device of this type.

A treatment for venous valvular dysfunction in patients that have had their vein wall distended and their valves irreversibly damaged is needed. The treatment should involve autologous tissue such that an endothelial layer is present in blood contact and thrombosis due to low flow is not of concern. The treatment should be easily performed so that patients with tissue edema and ulcers can tolerate the intervention and heal the area being accessed. The treatment should be applicable to those patients who have had deep venous thrombosis, phlebitis, or other vascular trauma and have irreversibly lost venous valvular function.

SUMMARY OF THE INVENTION

The present device and method for forming a venous valve overcomes the disadvantages of prior art prosthetic venous valves constructed out of crosslinked biological tissue, polymeric, or other biomaterials and it also overcomes problems associated with the surgical repair of venous valves. The venous valve of the present invention is constructed directly from the distended vein of a patient and it does not require the presence of an existing venous valve. Since the valve of the present invention is being constructed from autologous vein tissue with the natural endothelium of the vein in immediate contact with the blood, thrombosis such as that associated with biologic, polymeric, or other biomaterial constructed prosthesis is not a major concern. The venous valve of the present invention is configured from a segment of distended vein forming a new venous valve within the distended vein. Problems associated with irreversible valvular destruction or adhesion to the vessel wall due to deep venous thrombosis, phlebitis, or other vascular trauma will not influence the formation of the valve of the present invention within a distended vein. The method of forming the venous valve of the present invention is intended to be much simpler than venous valve bypass, valvular transposition, or valvuloplasty as performed by the peripheral vascular surgeon. The present method of forming the venous valve is intended to require only a minimally invasive surgery involving an easier and direct surgical procedure that can be applied to almost any distended vein.

The venous valve of the present invention involves identifying a segment of cylindrical tubular shaped distended vein and forming it into a venous conduit with a working valve in it. The venous valve has an overlap region that contains a through-flow member to allow antegrade blood flow through the venous valve and a sinus member which provides a cavity that is filled during the initiation of retrograde flow. A single valve cusp is located between the overlap through-flow member and the overlap sinus member. The valve cusp is capable of moving toward the sinus member to allow antegrade flow and moving to block the through-flow portion during the initiation of retrograde or back flow. The venous valve can also have an inlet transition region and it can have an outlet transition region. The transition regions are intended to provide a gradual tapering of the blood flow path from the distended vein to the smaller diameter of the overlap region. The blood flow surface of the through-flow and sinus portions of the overlap region, the transition regions, and the valve cusp are all endothelialized with the natural endothelium found in the native distended vein.

The structure of the venous valve is most easily and clearly described using cylindrical coordinates to describe the native distended vein and its relationship to various aspects of the venous valve that is formed from it. A cross section taken through the distended vein on the inlet side of the venous valve and facing downstream can be assigned a zero degree radian that intersects with the vein wall at a zero degree wall. Similarly one can identify a 90, 180, 270, or another degree wall along the vein wall at the inlet end of the overlap region. A zero degree line can be identified as that portion of the distended vein wall that extends axially and passes through the zero degree wall. The zero degree line describes venous wall material that may be sewn, sutured, stapled, bonded by adhesive, or attached in another way to another portion of venous wall material. The zero degree line can include the inner or outer surface of the vessel wall or it can include the entire vessel wall. Similarly, 90, 180, and 270 degree lines can also be identified. A first quadrant can be identified as the venous vessel wall that extends from the zero degree line to the 90 degree line. Similarly, a second, third, and fourth quadrant can also be identified.

For ease of describing the present invention, the vessel wall has been divided into quadrants, however it is understood that the vessel could be divided into a much greater number of sectors, each sector describing a smaller angle than 90 degrees and a smaller wall surface area than is occupied by a quadrant. Also, for ease of understanding, a wall line has been defined for the purposes of the drawings as extending approximately parallel to the centerline or axis of a tubular vessel. It is understood that for the venous valve of the present invention that a wall line is only required to have a component in the axial direction.

The venous valve of the present invention is intended to direct blood flow in a single antegrade direction from upstream to downstream, from its inlet to its outlet, toward the heart. The overlap region of this invention has an inlet and outlet end and an axial overlap length. In one embodiment of the present invention a segment of distended vein with an axial overlap length is identified. The zero degree line of the vein is brought into contact with the 180 degree line and the vein walls are attached using an attachment means which includes suturing or sewing, staples, adhesives or other bonding agents, thermal or other forms of welding, or other physical or chemical attachment mechanisms. It is understood that reference to the zero degree line, 180 degree line or other degree lines, points, or quadrants are approximate references and deviations from these lines, points, or quadrants are allowed within the framework of the present invention. For ease of understanding the invention is being described such that a wall line extending approximately parallel to the axis and extending throughout the overlap region is attached to another parallel wall line. It is understood that the wall lines need not be parallel to the axis and they need not extend throughout the overlap region to describe the present invention. To describe the present invention only a portion of such a wall line need be attached to a portion of another wall line. The 90 and 270 degree lines are brought into contact and the walls are attached using attachment means. At the inlet end of the overlap region, the first, second, and fourth quadrants are attached using attachment means. At the outlet end of the overlap region, the first and fourth quadrants are attached together.

The overlap region has a through-flow member defined by the third and fourth quadrant. At the outlet end of the overlap region is an opening between the first and second quadrant that provides entry into the sinus member of the overlap region. The first and fourth quadrant which are attached at the outlet end of the overlap region serve as the valve cusp. This attachment is not required to occur at the outlet end of the overlap region. It is understood that a portion of the first and fourth quadrants are attached together to form a member of the valve cusp. The cusp moves into approximation with the second quadrant during antegrade flow, and moves into approximation with the third quadrant during the initiation of retrograde or back flow allowing the sinus cavity or member to fill with blood. During antegrade blood flow through the venous valve, blood is directed through the through-flow member from the inlet to the outlet of the overlap region. This occurs for example in the legs during muscular contraction associated with walking or running or when the leg is in a reclined position and the pulsing of the heart moves the blood throughout the body including blood return from the legs. During the period of time that blood is not moving in an antegrade direction such as during standing or between periods of muscle contraction, blood is prevented from moving in a retrograde direction or from backflow or reflux by the venous valve. At the outlet end of the overlap region some backflow will go into the sinus member of the venous valve causing the sinus member to fill. This occurs as retrograde blood flow through the through-flow member generates fluid shear stresses upon the valve cusp causing it to move in the direction of flow. Due to geometrical constraints of the valve cusp with the inner and outer walls of the overlap region, the valve cusp also moves away from the second quadrant and allows blood to enter the sinus member of the overlap region. A small pressure difference between the blood at the inlet end of the sinus member and the outlet end of the sinus member which is dead ended and will not allow further retrograde blood flow, provides the driving force for blood entry into the sinus member. The valve cusp will move toward the third quadrant causing the through-flow member to close and stop further backflow or retrograde flow.

The four quadrants of the overlap region can be supported either within the walls or on the surface of the walls to resist possible stretching. A suture, thread, ribbon or other supportive means can be sewn, sutured, bonded, or placed along the third quadrant of the through-flow member at the inlet end to ensure that the entrance to the overlap region does not enlarge with continued exposure to pressure. Similarly, a supportive means can be attached to or placed along the second quadrant of the sinus member or the third quadrant of the through-flow member at the outlet end to ensure that further venous distension does not prevent the valve cusp from providing closure to the through-flow member. Additionally, further supportive means can be placed throughout any of the four quadrants to support both the through-flow member and sinus member.

The venous valve of the present invention can have an inlet transition region to connect the inlet end of the overlap region to the cylindrically shaped distended vein and an outlet transition region to connect the outlet end of the overlap region to the cylindrically shaped distended vein. These transition regions provide a tapered shape for blood to follow from the large distended vein to the smaller diameter for the through-flow member of the overlap region and back to the large diameter of the distended vein. Several possible ways of forming the transition regions are possible and are provided in the present invention in various embodiments to the invention.

The inlet transition region will be described at a location adjacent to the inlet end of the overlap region and at a location approximately half way between the inlet end of the overlap region and the cylindrically shaped native distended vein. Near the inlet end of the overlap region, the transition region has its zero degree wall in approximation to the 180 degree wall, and the 90 degree wall is in contact with and attached to the 270 degree wall. At the location halfway between the overlap region and the cylindrically shaped vein, approximately the 45 degree wall is attached to the 315 degree wall. This provides approximately a linear tapering of the diameter of the inlet transition region from the overlap region to the cylindrically shaped vein. It is understood that attachments can be made continuously along the transition region, not just at the two points that have been identified. Any excess material from the first and fourth quadrant that extends into the lumen of the transition region or extends out from the lumen of the transition region can be trimmed off or removed, provided that a leak tight attachment has been made along the transition region. The outlet transition region can be constructed in a manner similar to that of the inlet transition region.

An alternate method of constructing the inlet transition region again can be examined at two locations with interpolation or extrapolation of the results to other locations along the transition region. At the junction of the inlet transition region with the inlet end of the overlap region the zero degree point is in contact with and attached to the 180 degree point and the first quadrant can be attached to the second quadrant. At a location approximately half way between the inlet end of the overlap region and the cylindrically shaped distended vein, the 45 degree point is in contact with and attached to the 135 degree point. It is anticipated that a continuum of points are attached along the transition region such that a generally tapered shape for the transition region is formed from the overlap region to the cylindrically shaped vein.

In another embodiment for forming the overlap region, a segment of cylindrically shaped distended vein is placed into a flattened conformation and the first and fourth quadrants are attached together along the inlet end of the overlap region and cut at the inlet end of the overlap region through the first and fourth quadrant. Similarly, the distended vein is attached together along the outlet end of the overlap region and cut through the first and fourth quadrants of the outlet end of the overlap region. The zero degree line is placed into contact with and attached to the 180 degree line from the inlet end to the outlet end of the overlap region. This is accomplished by inverting the first and fourth quadrants into the second and third quadrants. This forms two separate tubes in the overlap region, one for through flow of blood between the third and fourth quadrant and one to serve as the sinus member of the overlap region between the first and second quadrant. At the inlet end of the overlap region the first and second quadrants are attached together. This is necessary to prevent antegrade blood flow from entering into the sinus member of the overlap region. The 90 and 270 degree lines are attached together from the inlet end to the outlet end of the overlap region to hold the sinus member into immediate contact with the through-flow member of the overlap region. This provides a single lumen between the third and fourth quadrant for through flow through this member of the overlap region. At the outlet end of the overlap region is located the leading edge of the single valve cusp that is made up of the first and fourth quadrants of the overlap region. The valve cusp is completely endothelialized along with all blood contact surfaces of the venous valve. The inverted nature of the leading edge provides this embodiment with a particularly good resistance to thrombosis. The walls of the valve can be supported as described earlier with the other embodiments.

The inlet transition regions for the embodiment just discussed can be formed by attaching the first and fourth quadrants together on a line that extends from a point of attachment of the 90 and 270 degree walls at the inlet end of the overlap region along a beveled pathway to a zero degree wall on the cylindrically shaped distended vein. The beveled or tapered pathway provides a smooth blood flow transition from the distended vein to the overlap region. Any excess venous tissue that extends from the beveled attachment line to the zero degree line in the transition region can be trimmed off or removed. The outlet transition region can be similarly constructed.

It is noted that the construction of the venous valve of this invention requires some means for attachment between various quadrants of the venous wall. In forming the attachment of the zero degree line with the 180 degree line of the first embodiment, or attaching one quadrant to another along an inlet or outlet end of the overlap region, or for forming many other of the wall attachments or wall cuts, the distended vessel can be placed in a flattened position to allow the attachments to be made easier. The venous valve of this invention lends itself well to a mechanism that will assist the surgeon in making the attachments and cuts and allow the formation of this venous valve to be made quickly and consistently.

It is understood that the inlet and outlet transitions region embodiments can be interchanged with each other when possible. It is understood that other possible variations of the overlap region or transition regions may exist that are not shown by the drawings but are indeed taught by this patent application and should be considered as part of the teachings of this disclosure. The teachings of this patent application are not limited to the drawings and embodiments included herein.

It is further understood that the venous valve of the present invention can be constructed out of biological tissue such as venous tissue from animal sources, autologous tissue such as pericardium or venous tissue from another part of the body, or polymeric materials such as those used in vascular grafts. A venous valve of the present invention can be constructed as per the methods taught in the present disclosure and the resultant venous valve can be implanted interpositionally into a vein of a person at the venous site that requires a functioning venous valve. An embodiment such as this provides the advantage of simplicity of design and ease of formation.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
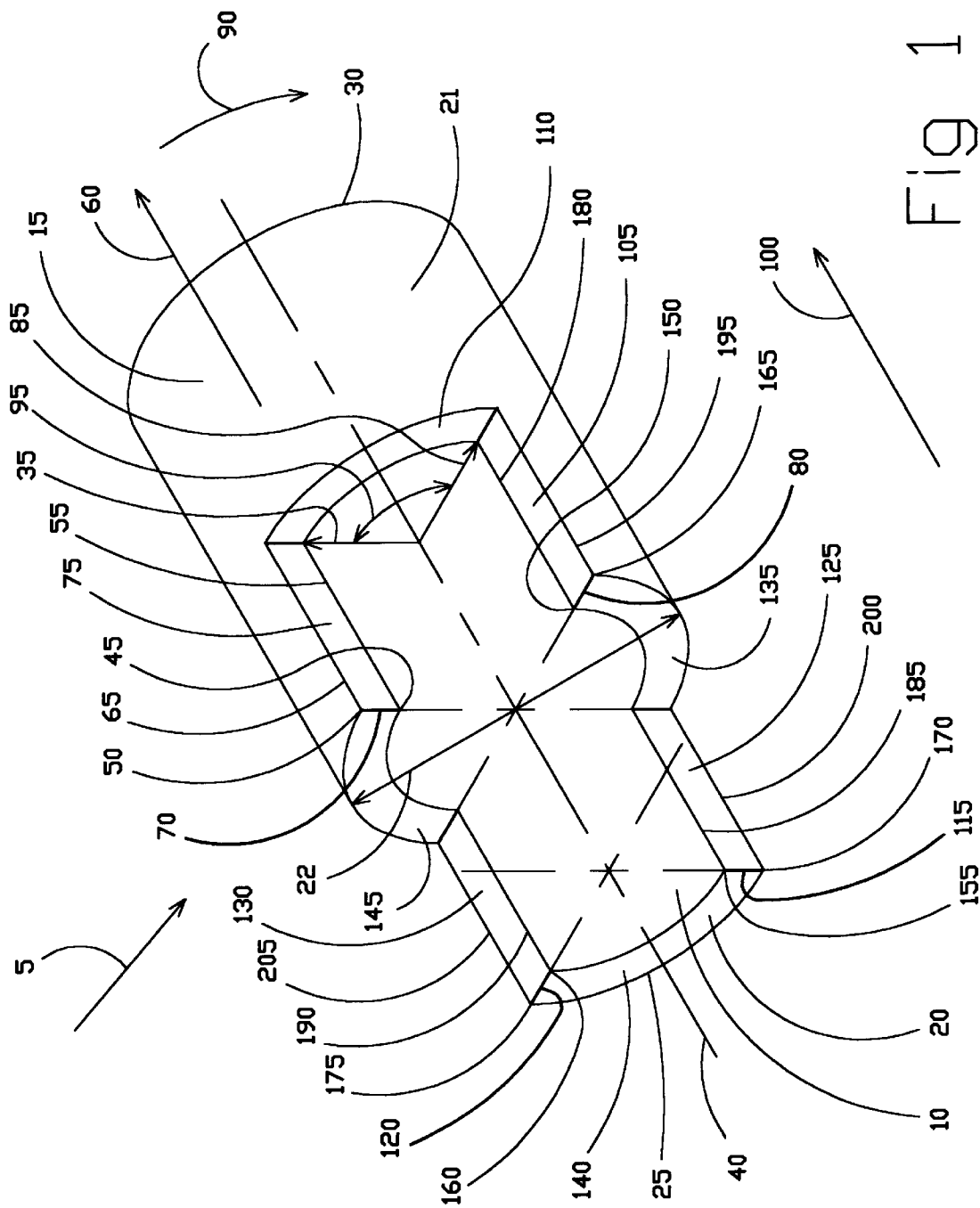
FIG. 1 is an isometric view of distended vein segment.

An embodiment of the venous valve of the present invention is formed from an approximately cylindrically shaped segment of distended native vein and the formation occurs with the vein in place in its naturally occurring in situ position. Once the venous valve has been formed, it can be contiguous with or it can be attached to native vein tissue both upstream and downstream from the venous valve. The structure of the venous valve and the methods for its construction are most easily and accurately described by referring to a cylindrical coordinate system to describe various properties or characteristics of the native vein and apply these characteristics to the formation of the venous valve of the present invention.

A venous valve of an embodiment of the present invention could also be formed from a segment of vein or other tissue taken from any suitable location within the same patient that requires the venous valve. The segment of vein containing the valve formed by the methods of the present invention could then be transsected from its natural venous location or other location and interposed into the autologous vein that requires the venous valve. Autologous tissue such as pericardium or other tissue conduits could also be used to form the venous valve of the present invention. Pericardial tissue could be formed into an approximate cylindrical shape or tubular shape and formed into the vein of the present invention as described by the present disclosure. Such a formed venous valve would be implanted by standard interpositional surgical procedure into the vein of a patient requiring a venous valve by simply transsecting a portion of the patients vein and interposing a segment of tissue containing a valve formed by the present invention into its place using standard surgical technique or other less invasive technique. A venous valve of the one described in the present invention could also be formed out of biological tissue obtained from an animal venous conduit, a venous conduit from another human, other suitable conduit, pericardial tissue, or other suitable tissue. Such tissue could be treated using a crosslinking agent such as glutaraldehyde or other crosslinking or strengthening agent to enhance strength and reduce the antigenic character of the tissue. The biological tissue or tissue conduit could then be formed into a venous valve using the methods described in the present invention. The formed venous valve of the present invention could then be interposed into the vein of a patient requiring a venous valve. The venous valve of the present invention could also be formed out of polymeric or a composite material including polymers, metals, ceramics, or other biologically compatible materials. Such polymeric or composite materials could be formed into an approximately tubular shape and further formed into the venous valve of the present invention using the methods taught in this disclosure. Such tubular means from which the venous valve of the present invention can be constructed therefore include autologous vein, autologous tissue formed into a tubular shape of approximately round or other cross sectional shape, non-autologous biological conduit, non-autologous biological tissue, polymeric conduit, polymeric fabric, polymeric sheeting, or polymeric material formed into a conduit, or a composite material conduit.

FIG. 1 is an isometric view of a distended vein segment 5 or other tubular conduit that can be formed into the venous valve of this invention with an inner surface 10, an outer surface 15, a vein wall 20, a wall area 21, and a distended vein segment diameter 22. The distended vein segment 5 can be formed into the venous valve of the present invention. The distended vein segment 5 can also be transsected and replaced by a venous valve of the present invention formed from another suitable biocompatibe material formed into a tube and being described by similar nomenclature. The distended vein segment 5 is shown extending from an inlet vein-transition junction 25 to the outlet vein-transition junction 30. The distended vein segment 5 is a portion of the autologous vein that requires a venous valve. At or near the inlet vein-transition junction 25 is found a zero degree radian 35 extending from a centerline 40 through an inner surface zero degree point 45 to an outer surface zero degree point 50. A cut-away view is shown in FIG. 1 to provide an easier understanding of the structure of the vein or other tubular structure and to establish a terminology that will be used later to describe the present invention. An inner surface zero degree line 55 is a line that passes along the inner surface 10 of the vein and travels generally parallel to the centerline 40 in an axial direction passing through the inner surface zero degree point 45. Similarly, an outer surface zero degree line 65 is a line generally parallel to the centerline 40 and passes along the outer surface 15 through the outer surface zero degree point 50. The vein wall along the zero degree radian 35 extending from the inner surface zero degree point 45 to the outer surface zero degree point 50 is referred to as zero degree wall 70. A zero degree wall line 75 is defined as the zero degree wall 70 that follows the wall of the vein along a line generally in a direction parallel to the centerline 40 and passing through the zero degree wall 70. The zero degree wall 70 and zero degree wall line 75 are defined to allow an alternate description of attachment between two vein walls to be made. The zero degree wall line includes the inner 55 and outer 60 surface zero degree lines plus the wall in between. Attachment between a zero degree wall line 75 and a vein wall 20, for example, is understood to mean that either the inner surface 10, the outer surface 15, or the venous tissues between the inner 10 and outer 15 surfaces of the venous wall 20, or the vein wall 20 including both surfaces along the zero degree wall line 75 can be attached to another vein wall 20. In a similar manner a 90 degree wall 80 can be identified for the distended vein segment 5 at a location of intersection between a 90 degree radian 85 and the vessel wall 20. The 90 degree radian 85 is rotated clockwise 90 about the centerline 40, an angle 95 of 90 degrees from the zero degree radian 35 and with respect to an antegrade flow direction 100. A 90 degree wall line 105 can then be identified in a manner similar to that described for the zero degree wall line 75 and the vein wall 20 that extends between the zero 75 and 90 (105) degree wall lines is considered the first quadrant 110. Similarly, a 180 (115) and 270 (120) degree wall, a 180 (125) and 270 (130) degree wall line, and a second 135, third 140, and fourth 145 quadrant can be identified. In a manner similar to that discussed earlier, an inner surface 90 (150), 180 (155), and 270 (160) degree point and an outer surface 90 (165), 180 (170), and 270 (175) degree point can be defined. Similarly, an inner surface 90 (180), 180 (185), and 270 (190) degree line and an outer surface 90 (195), 180 (200), and 270 (205) degree line can be identified.

It is understood that the zero, 90, 180, and 270 degree lines for the inner surface, outer surface, and wall as they are discussed in this disclosure are not required to be exact but are used only for ease of understanding. Actual attachment lines for the valve of the present invention can vary from what is described in this disclosure by approximately 90 degrees or more depending upon the condition of the native distended vein, the accuracy of the procedure, and the ability of the present venous valve formation methods to allow for considerable modification without changing the overall teachings and finction of the valve. The description provided in FIG. 1 is intended to provide a simplified system to describe the device and method of formation of the present venous valve in an understandable way. The distended vein segment 5 was divided into quadrants for ease of description although it is understood that the vein segment could be divided into more numerous sectors (not shown), each sector having less than 90 degrees and having a wall surface area less than a quadrant. Although the quadrants used in this disclosure are positioned in a clockwise 90 manner, it is understood that the location of the first quadrant 110 was arbitrarily chosen. Individual sectors which could have been used to describe the venous valve of the present invention can be assigned arbitrarily about the distended vein segment 5 to describe the line and wall attachments of the present invention. It is further within the understanding of the present invention that a portion of an inner 10 or outer 15 surface or wall area 21 of a quadrant or a sector could be attached to a portion of an inner 10 or outer 15 surface or wall area 21 of another quadrant over a specific area without changing the function of the venous valve. Such a surface attachment or a wall area attachment is understood to be included within the teachings of the present invention. It is also understood that an attachment of an inner or outer surface line or a wall line to another surface or wall line involves more of the vein wall than simply a line. It is assumed that a portion of the vein wall 20 on each side of such a line attachment is involved in the attachment in order to provide strength to the attachment. A surface line attachment or a wall line attachment therefore is understood to involve a wall area 21 in forming the attachment.

Figure 2:
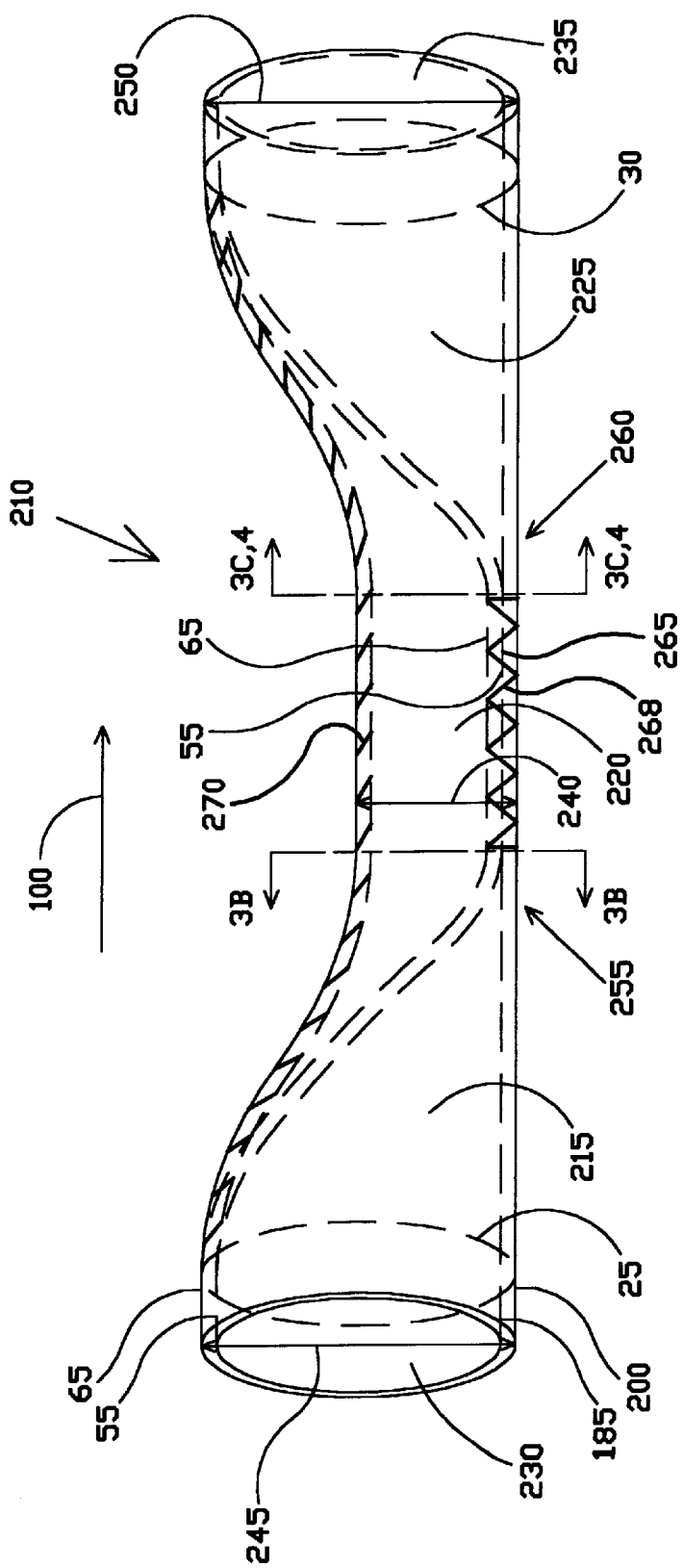
FIG. 2 is an isometric view of a first embodiment of the venous valve of this invention.

FIG. 2 is an isometric view of a first embodiment of the venous valve 210 of the present invention. The venous valve of this embodiment is made up of three separate regions, the inlet transition region 215, the overlap region 220, and the outlet transition region 225. The venous valve 210 of one embodiment is joined contiguously to the inlet distended vein 230 at the inlet vein-transition junction 25 and to the outlet distended vein 235 at the outlet transition-vein junction 30. The overlap transverse dimension 240 is smaller than the inlet distended vein diameter 245 or the outlet distended vein diameter 250. The inlet transition region 215 provides a smooth blood flow transition in an antegrade flow direction 100 from the larger inlet distended vein diameter 245 to the smaller overlap transverse dimension 240 at the overlap inlet end 255. The outlet transition region 225 provides a smooth blood flow transition in the antegrade flow direction 100 from the overlap outlet end 255 to the outlet transition-vein junction 30. In the overlap region 220, the inner surface zero degree line 55 is shown in contact with the inner surface 180 degree line 185, and having an inner surface zero and 180 degree line attachment 265. This inner surface zero and 180 degree line attachment 265 can involve a surface attachment method such as a thermal or laser weld, a biological glue or adhesive, or other surface attachment means. Additionally, the inner surface zero and 180 degree line attachment 265 in the overlap region 220 can involve the entire vessel wall, by attaching the zero (75) and 180 (125) degree wall lines with sutures, staples, or any other wall attachment means including laser, thermal, or other fusion methods that will attach the zero degree wall line 75 and the 180 degree wall line 125 together in the overlap region 220. An example of such means 268 is shown in FIG. 2 extending in the overlap region 220. This inner surface zero and 180 degree line attachment 265 is shown to extend from the overlap inlet end to outlet end but it is understood that it can extend over only a portion of this overlap region 220 without affecting the finction of the valve of the present invention. The outer surface zero 65 and 180 (200) degree lines are also shown. An outer surface 90 and 270 degree line attachment 270 is also present in the overlap region 220. This outer surface 90 and 270 degree line attachment 270 can be made by attaching the outer surfaces together using thermal or laser bonding methods or with biological glues or adhesives. Outer surface 90 and 270 degree line attachment 270 can also be made using sutures, staples, fusion methods, or other attachment means to attach the 90 degree wall line 105 to the 270 degree wall line 130 with attachment extending through a portion of or through the entire vessel wall 20. This outer surface 90 and 280 degree line attachment 270 can be intermittant and can extend over only a portion of the length of the overlap region 220 without affecting the function of the venous valve of the present invention.

Figure 3A:
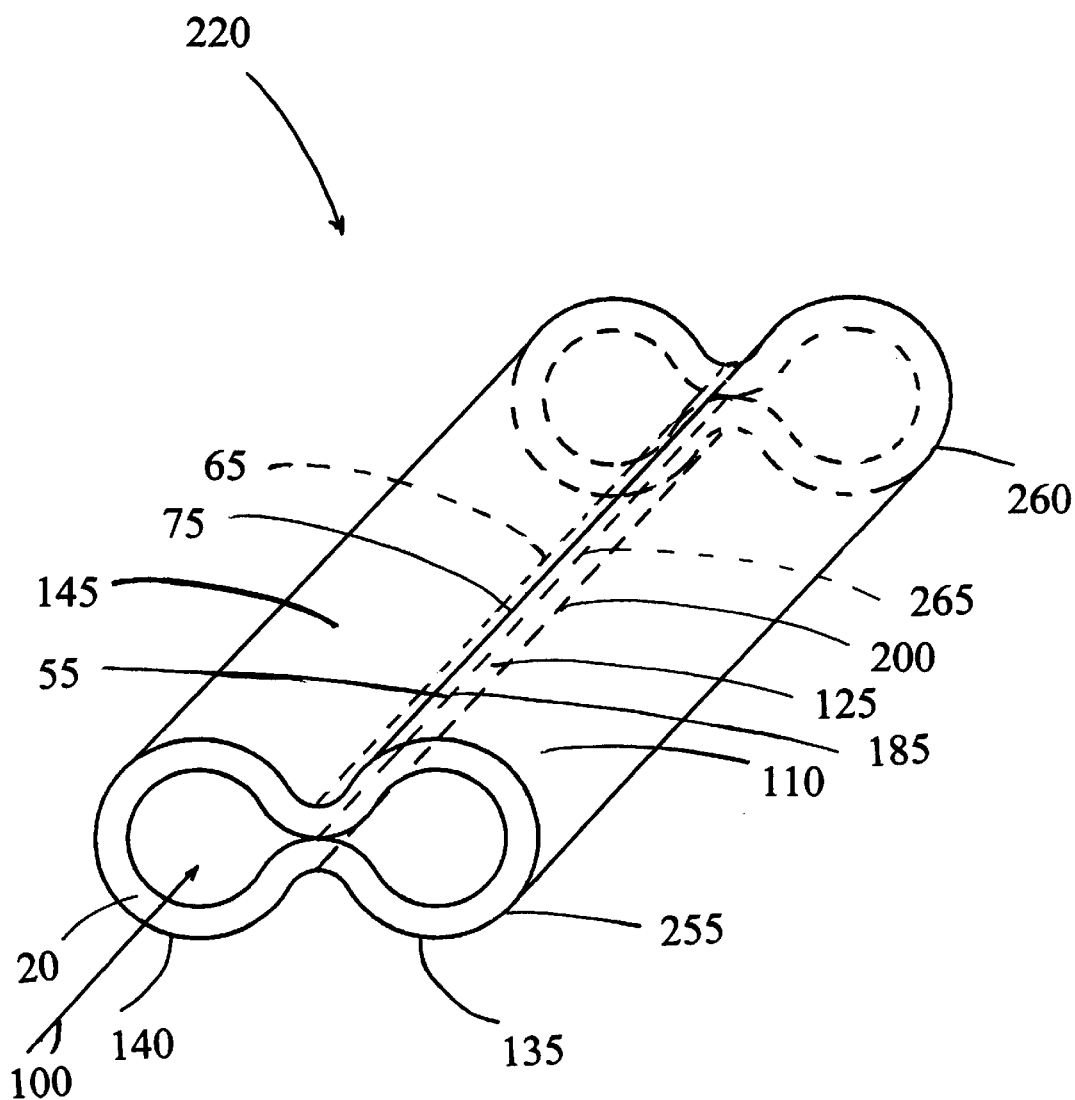
FIG. 3A is an isometric view of an overlap region in an early stage of formation.

FIG. 3A is an isometric view of the overlap region 220 of one embodiment of the venous valve of the present invention in an early stage of formation. The vein wall 20 that is to form the overlap region 220 between the overlap inlet 255 and outlet 260 end has been partially flattened by allowing the first 110 and fourth 145 quadrant to be positioned above the second 135 and third 140 quadrant, respectively. This allows the zero degree wall line 75 to lie directly upon the 180 degree wall line 125 and allow ease of surface or wall attachment means to hold the inner surface zero degree line 55 against the inner surface 180 degree line 185. The outer surface zero 65 and 180 (200) degree line and the antegrade flow direction 100 are shown. It is understood that the overlap region 220 may be flattened to a greater extent than is shown in FIG. 3A prior to forming the inner surface zero and 180 degree line attachment 265.

Figure 3B:
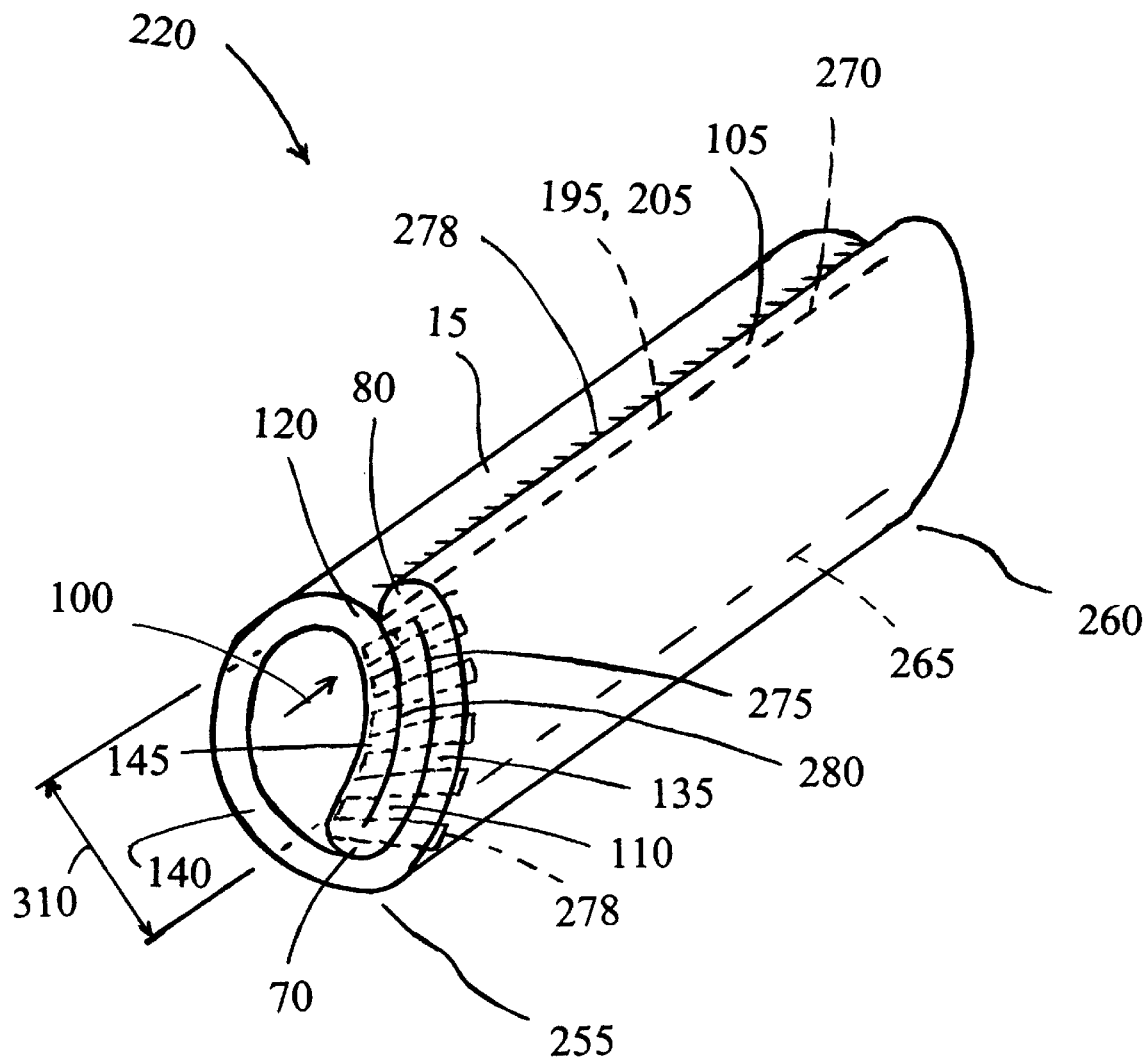
FIG. 3B is an isometric view of an overlap region from an inlet end.

FIG. 3B is an isometric view of the overlap region 220 showing the overlap inlet end 255 of the venous valve 210 of this invention. The inner surface zero and 180 degree line attachment 265 extends from the overlap inlet end 255 to the overlap outlet end 260; this divisional attachment divides the overlap region into two tubular members, one member between the first 110 and second 135 quadrants, and another member between the third 140 and fourth 145 quadrants. The two tubular members provide two separate lumens or compartments without leakage of blood across the divisional attachment. Such a divisional attachment could be formed by attachment of two sectors together instead of quadrants as shown in the drawings for ease of description. An overlap inlet end first and second quadrant attachment 275 at the overlap inlet end forms a closure attachment that prevents blood flow in an antegrade flow direction 100 from entering between the first 110 and second 135 quadrant. This overlap inlet end first and second quadrant attachment 275 can be made by attaching the inner surface 10 of the first 110 and second 135 quadrant using surface attachment means such as bonding agents or welding methods as described earlier or attachment can be made through the vein wall 20 of the first 110 and second 135 quadrants using sutures, staples, fibers, or other wall attachment means. An example of such surface or wall attachment means 278 is shown in FIG. 3B, and can be formed of a suture or other material. An overlap inlet end first and fourth quadrant attachment 280 is also found at the overlap inlet end 255; this attachment 280 prevents antegrade blood flow from entering between the first 110 and fourth 145 quadrants. This overlap inlet end first and fourth quadrant attachment 280 forms a portion of the valve cusp attachment that is required to hold the walls of the first 110 and fourth 145 quadrants together over at least a portion of the wall. This overlap inlet end first and fourth quadrant attachment 280 can be made by attaching the outer surfaces 15 of the first 110 and fourth 145 quadrants from the 270 (120) and 90 (80) degree wall to the zero degree wall 70 using surface attachment means on the outside surfaces of the first 110 and fourth 145 quadrants or using wall attachment means that attach the vein wall of the first 110 and fourth 145 quadrants together at the overlap inlet end 255. The first 110, second 135, and fourth 145 quadrants can all be attached together at the overlap inlet end 255 using a single surface or wall attachment means, an example of which is shown by reference numeral 278. Attachment of the outer surface 90 (195) and 270 (205) degree lines from the overlap inlet end 255 to the overlap outlet end 260 holds the outer surfaces 15 of the first 110 and fourth 145 quadrants into approximation with each other throughout the overlap region 220 and forms an approximation attachment. The 90 degree wall line 105 can be attached to the 270 degree wall line of the overlap region 220 using attachment means including sutures, staples, or fusion methods. An example of such attachment means 278 is shown in FIG. 3B, and can be formed of suture or other material.

The overlap inlet end 255 is shown as a transverse section that extends in a direction perpendicular to the antegrade flow direction 100. It is understood that the overlap inlet end can be positioned on a bevel or at an angle with respect to the direction of flow in an antegrade direction 100. Additionally, the overlap inlet end first and second quadrant attachment 275 is not required to be located in immediate apposition to the overlap inlet end first and fourth quadrant attachment 280. All reference numerals correspond to those elements previously or otherwise described.

Figure 3C:
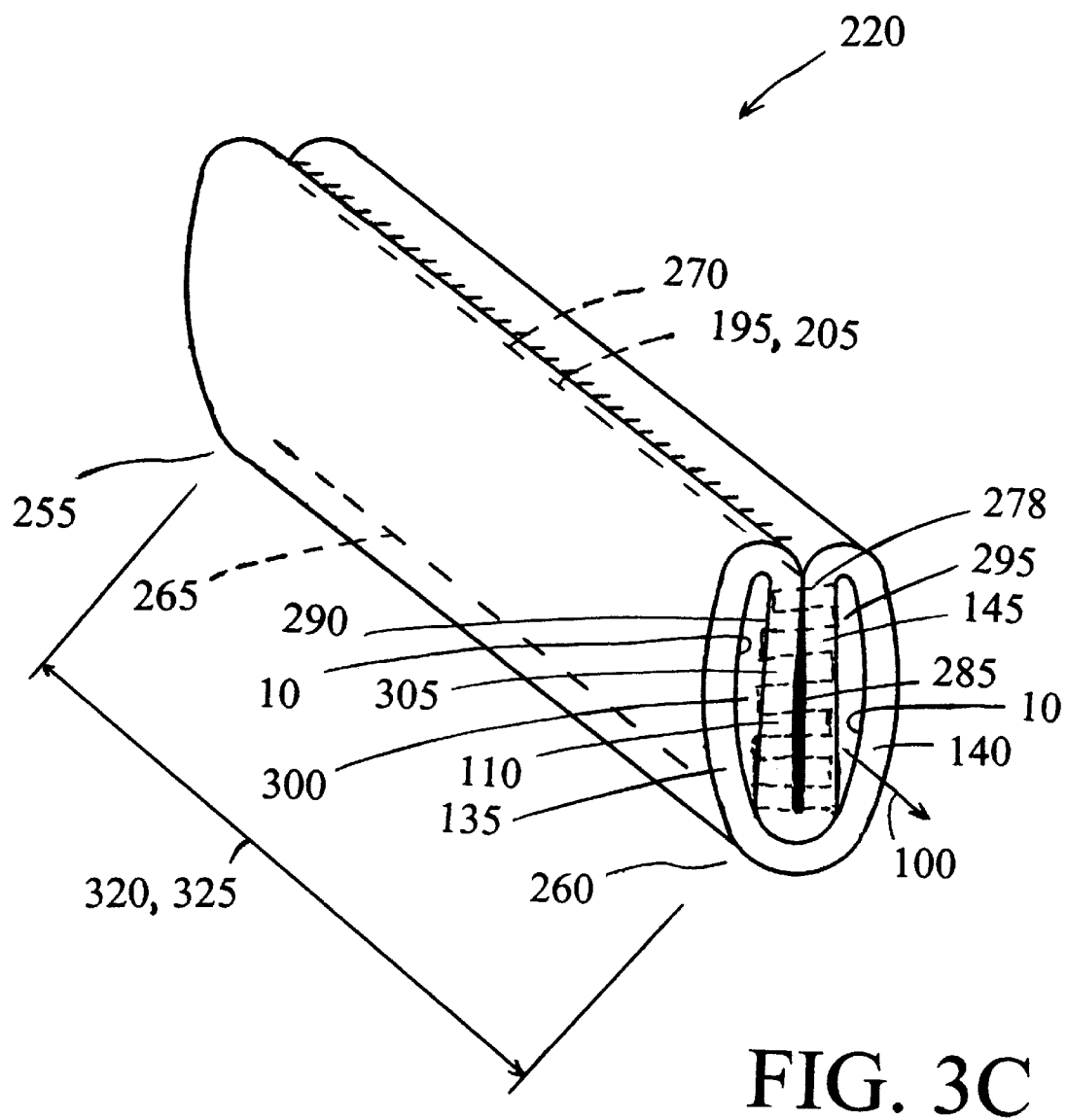
FIG. 3C is an isometric view of an overlap region from an outlet end.

FIG. 3C is an isometric view of the overlap region 220 showing the overlap outlet end 260 of the venous valve 210 of the present invention. At the overlap outlet end 260, an overlap outlet end first and fourth quadrant attachment 285 is formed to attach the inner surfaces 10 (see FIG. 1) of the first 110 and fourth 145 quadrants along the overlap outlet end 260. This overlap outlet end first and fourth quadrant attachment 285 can be made using bonding agents, biological glues, or other adhesives, or it can be formed from a thermal, laser, or fusion process, or other surface method that bonds tissue surfaces or tissue walls together. The overlap outlet end first and fourth quadrant attachment 285 can also be formed by sewing or suturing the vein walls together along the overlap outlet end or by using staples or other wall attachment means. An example of such surface or wall attachment means 278 is shown in FIG. 3C, and can be formed of suture, staples, metallic or polymeric fibers, or other material. Laser fusion, thermal fusion, and other fusion methods can also be considered wall attachment means since they can extend into the central tissue found in the vein wall to achieve their attachment. The overlap outlet end first and fourth quadrant attachment 285 along with the overlap inlet end first and fourth quadrant attachment 280 (see FIG. 3B) form a valve cusp attachment that identifies one way of attaching the first 110 and fourth 145 quadrants together. Such a valve cusp attachment can be formed using attachment means to hold a portion of the inner surfaces 10 of the first 110 and fourth 145 quadrants together or hold a portion of the walls of the first 110 and fourth 145 quadrants together such that they are attached and can function as a valve cusp 290. All reference numerals correspond to those elements previously or otherwise described.

The outer surface 90 and 270 degree line attachment 270 is shown holding the outer surface 90 degree line 195 in contact with the outer surface 270 degree line 205 from the overlap inlet end 255 to the overlap outlet end 260. This outer surface 90 and 270 degree line attachment 270 is an approximation attachment and is not required in this embodiment to be continuous and can have intermittent attachments as long as the outer surfaces 15 of the first 110 and fourth 145 quadrants are held in apposition with each other in the overlap region 220. The inner surface zero and 180 degree line attachment 265 is shown in FIG. 3C to extend from the overlap inlet end 255 to the overlap outlet end 260 and this divisional attachment could involve only a portion of the overlap region 220 as long as it forms two tubular members as shown in FIG. 3C within the overlap region 220 that do not leak substantial blood flow across this attachment 265. An overlap through-flow member 295 is formed by the third 140 and fourth 145 quadrants of the overlap region 220 providing a passage for blood flow in an antegrade flow direction 100. An overlap sinus member 300 is formed by the first 110 and second 135 quadrants of the overlap region 220. The second 135 and fourth 145 quadrants which are attached at the overlap outlet end first and fourth quadrant attachment 285, form the valve cusp 290 with a commissure 305 or leading edge of the valve cusp 290 located at the overlap outlet end first and fourth quadrant attachment 285. During blood flow in an antegrade direction 100, the valve cusp 290 is displaced toward the second 135 quadrant and the inner surface 10 (see FIG. 1) of the first quadrant 110 can come into contact with the inner surface 10 of the second quadrant 135. Movement of the valve cusp 290 during blood flow in an antegrade direction 100 provides a large overlap through-flow member diameter 310 and the least resistance to blood flow. Antegrade blood flow can occur in the veins of the leg during leg muscle contraction and with the legs in a reclined position. Initiaition of blood flow in a retrograde flow direction 315 in the overlap through-flow member 295 can initiate in the veins of the leg during leg muscle relaxation or during periods of standing. Retrograde flow of blood in a direction opposite to the antegrade flow direction 100 can create shear stresses on the inside surface of the fourth quadrant 145 causing the commissure 305 of the valve cusp 290 to move toward the third quadrant 140 with possibly some displacement toward the overlap inlet end 255 and away from the inner surface 10 of the second quadrant 135. Blood flow enters the overlap sinus member 300 due to a small pressure driving force that can be approximately 0.1 to 1 mm Mercury (Hg) from the overlap outlet end 260 to overlap inlet end 255 of the overlap sinus member 300. As blood fills the overlap sinus member 300 which is dead ended at the overlap inlet end 255, the valve cusp 290 is moved toward the third quadrant 140 of the overlap region 220. The valve commissure 305 comes into contact with or adjacent to the inner surface 10 of the third 140 quadrant of the overlap region 220 and stops any further blood flow in a retrograde direction 100 from occurring in the overlap through-flow member 295. For the valve commissure 305 to reach from the inner surface of the third quadrant 140 during antegrade flow, to the inner surface of the second quadrant during initiation of retrograde flow, the valve cusp length 320 should be at least approximately one half the overlap through-flow member diameter 310 (see FIG. 3B). The overlap region length 325 can be approximately the same length as the valve cusp length 320. Due to the formation methods for the overlap region 220 of the present venous valve embodiment, the overlap through-flow member diameter 310 can be approximately one half of the distended vein segment diameter 22 from which it has been formed, and the overlap region length 325 can be approximately at least one quarter of the distended vein segment diameter 22 from which it has been formed. The overlap region length 325 could be longer than one quarter of the distended vein segment diameter 22 and could be as large or larger than the distended vein diameter 22. An excessively long overlap region length 325 extending more than approximately ten times the through-flow member diameter 310 could have the disadvantage that the overlap sinus member 300 could have a tendency toward thrombosis due to blood stasis in that member. All reference numerals correspond to those elements previously or otherwise described.

It is understood that the venous valve 210 of the present invention is not required to be formed from a distended vein, and other materials of construction can also be used. It is further understood that the overlap region length 325 used in the previous discussion is used to provide an easily understandable estimate of a valve cusp length 320. The valve cusp 290 can be formed with a beveled outlet end (not shown), and is not required to have a valve cusp length 320 equal to the overlap region length 325.

Figure 4:
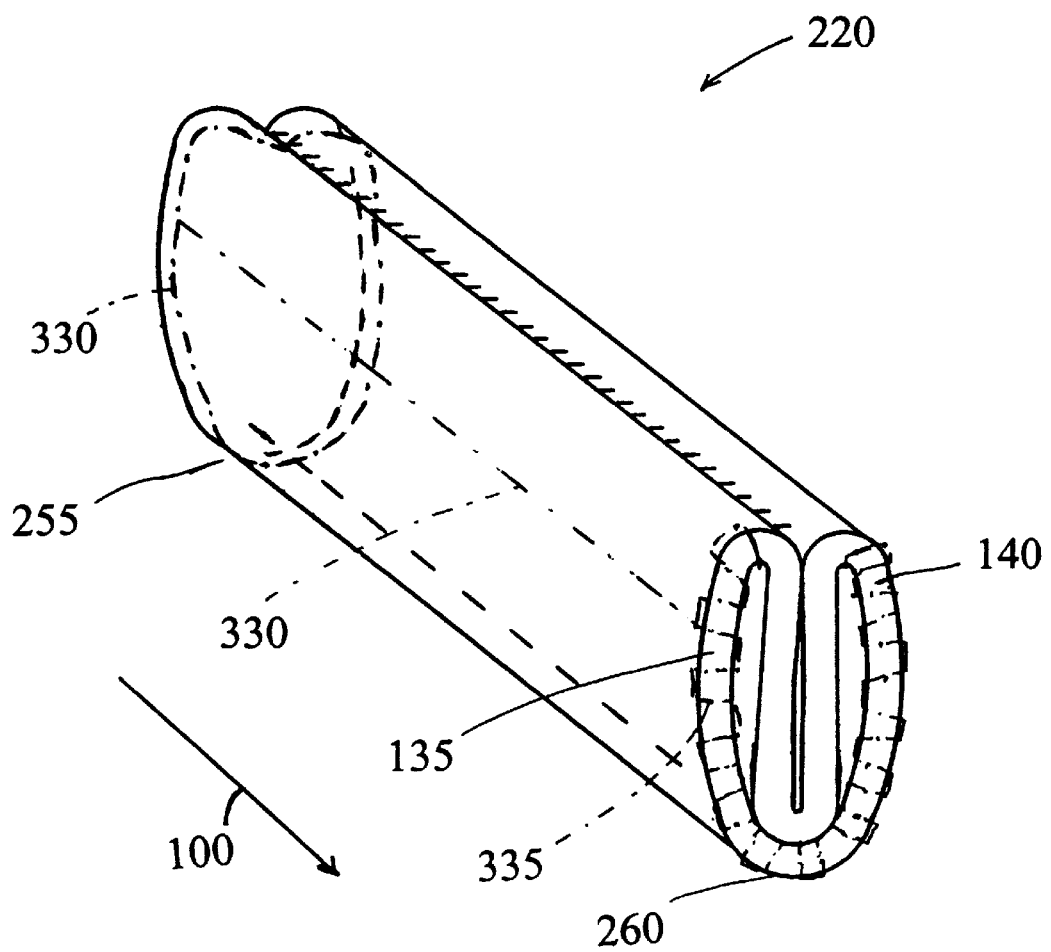
FIG. 4 is an isometric view of an overlap region with wall support.

FIG. 4 is an isometric view of the overlap region 220 showing external wall support 330 such as suture, metal wire, polymeric fiber, ribbon, or other wall support means being placed around the outside surface 15 of the second 135 and third 140 quadrants at the overlap inlet end 255. Internal wall support 335 such as suture, metal wire, polymeric fiber, polymeric ribbon, or other support means can also be placed within, sutured within, or placed through the vein wall as shown within the second 135 and third 140 quadrants at the overlap outlet end 260 or elsewhere throughout all or a portion of the venous valve of the present invention. Such internal 335 or external 330 wall support can help to resist distension of the overlap inlet 255 or outlet 260 end and ensure long term function of the venous valve of this invention. It is understood that internal 335 or external 330 wall support can be used at either or both the overlap inlet or outlet end. Internal 335 or external 330 wall support can also be used to support all four quadrant walls of the overlap region 220 throughout the entire overlap region 220 between the overlap inlet 255 and outlet 260 ends. Such internal 335 or external 330 wall support can extend within a transverse section of the overlap region 220 as shown in FIG. 4, it can extend axially 60 (see FIG. 1) in the antegrade flow direction 100, or it can have components in both directions. All reference numerals correspond to those elements previously or otherwise described.

Figure 5A:
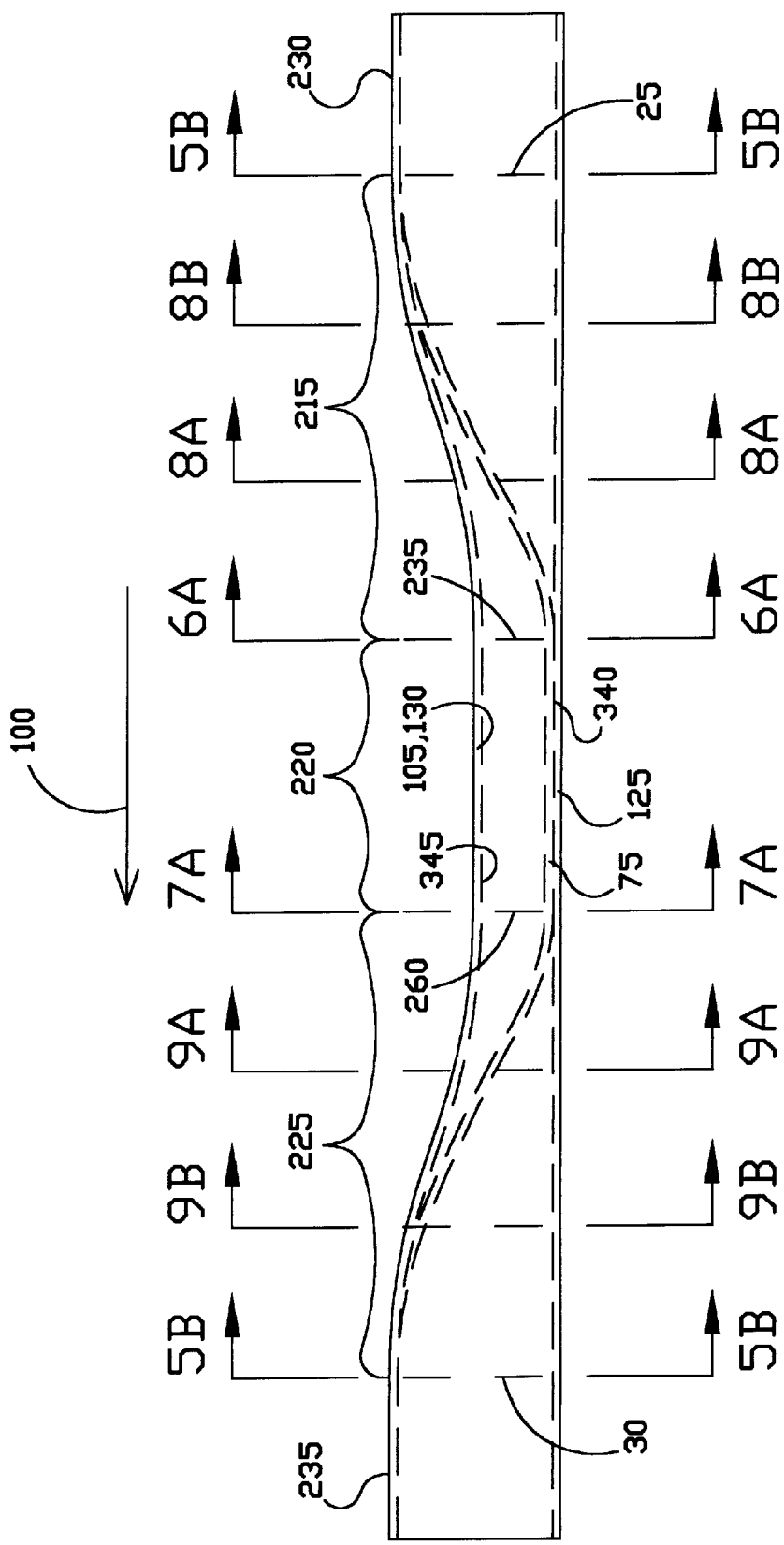
FIG. 5A is a partially sectioned view of the first embodiment of the venous valve of this invention in a flattened state.
Figure 5B:
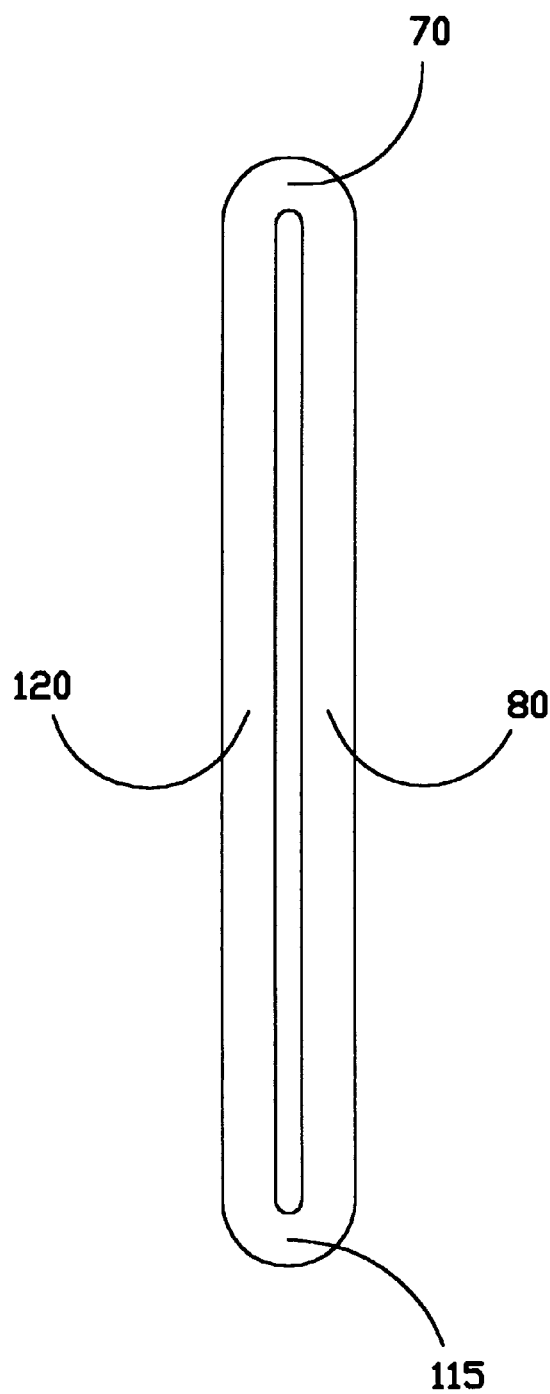
FIG. 5B is a sectional view of the inlet or outlet distended vein in a flattened state.
Figure 5C:
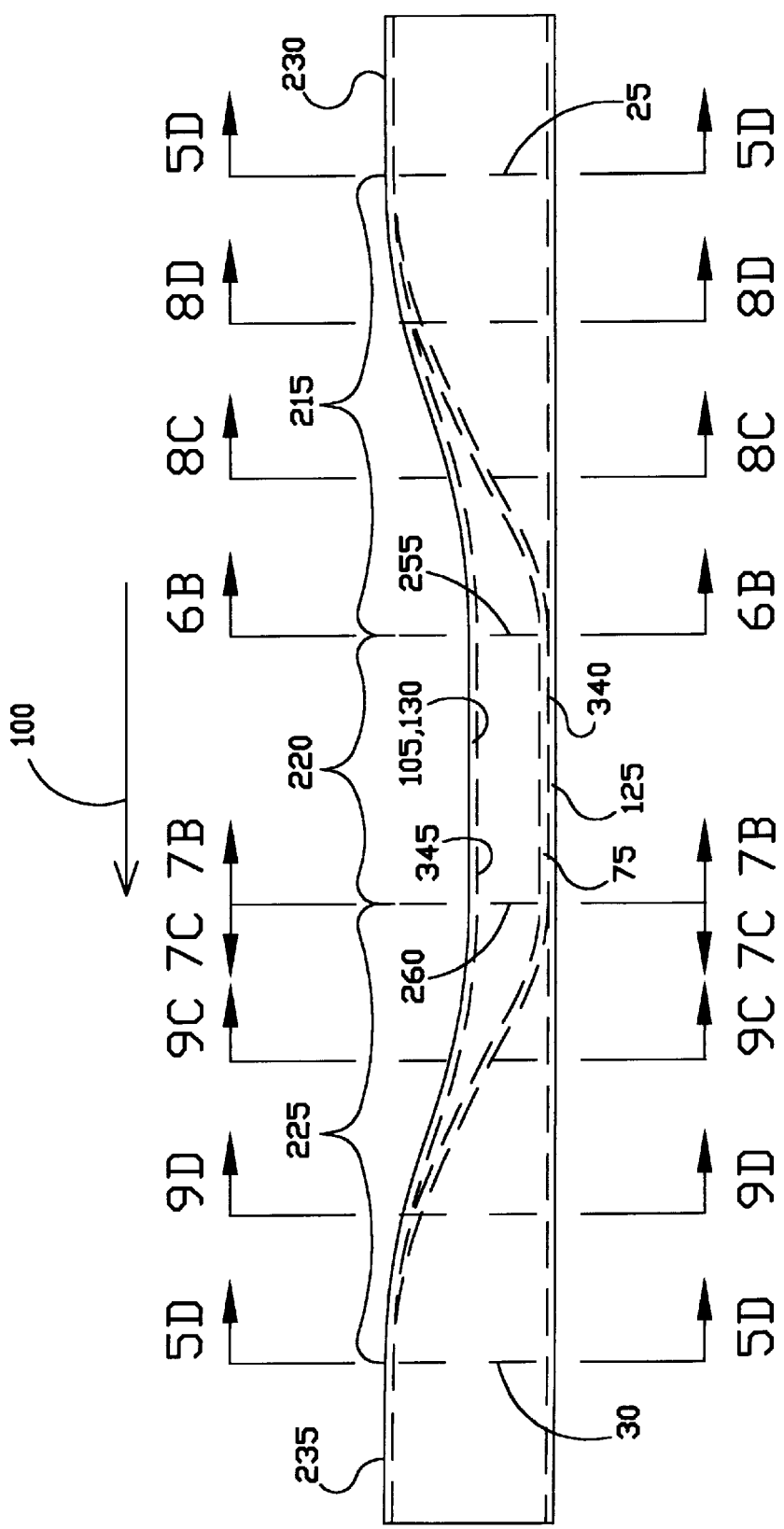
FIG. 5C is a partially sectioned view of the first embodiment of the venous valve of this invention conformed for blood flow.
Figure 5D:
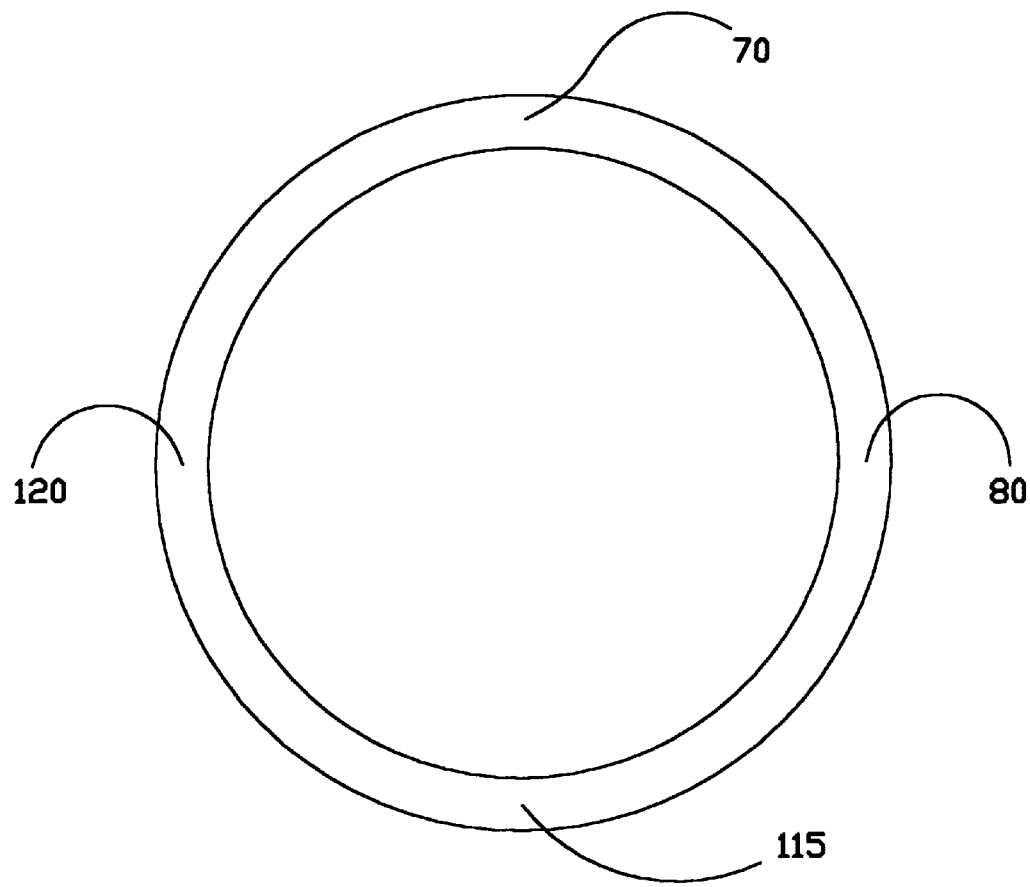
FIG. 5D is a sectional view of the inlet or outlet distended vein conformed for blood flow.

FIG. 5A is a partially sectioned view of an embodiment of the venous valve 210 of the present invention in a flattened condition as could be found during the formation of the venous valve. FIG. 5C is a partially sectioned view of an embodiment of the venous valve of the present invention with antegrade blood flow passing through it. Sectional views of the inlet 230 or outlet 235 distended vein are shown in a flattened conformation as can be found during venous valve formation in FIG. 5B and in a round conformation providing blood flow in FIG. 5D. FIGS. 5A–5D will be discussed collectively. The zero degree wall line 75 is attached to the 180 degree wall line 125 in the overlap region 220 forming an overlap zero and 180 degree wall line attachment 340 or divisional attachment. The 90 degree wall line 105 is attached to the 270 degree wall line 130 in the overlap region 220 forming an overlap 90 and 270 degree wall line attachment 345 or approximation attachment. The venous valve 210 of the present invention is shown to have an overlap region 220 which is contiguous with the inlet 215 and outlet 225 transition regions. These regions do not have to be contiguous; they can be attached together or portions of the vein wall 20 can be cut and removed as found in a later embodiment. The venous valve 210 of the present invention is only required to have an overlap region 220. The inlet 215 and outlet 225 transition regions provide smooth blood transition from inlet distended vein 230 to the overlap region 220 and from the overlap region 220 to the outlet distended vein 235, but are not required in the venous valve 210 of the present invention. The inlet transition region 215 can be contiguous with the inlet distended vein 230 if it is formed in situ from an existing native vein. Similarly, the outlet transition region 225 can be contiguous with the outlet distended vein 235. Alternately, an embodiment of the venous valve of the present invention extending from the inlet vein-transition junction 25 to the outlet transition-vein junction 30, or another embodiment extending only from the overlap inlet end 255 to the overlap outlet end 260 can be interposed surgically into a vein that requires a venous valve. The venous valve 210 of the present invention can also be constructed of biological tissue, polymeric material, or autologous tissue taken from another part of the anatomy and formed into the venous valve. All reference numerals correspond to those elements previously or otherwise described.

Figure 6A:
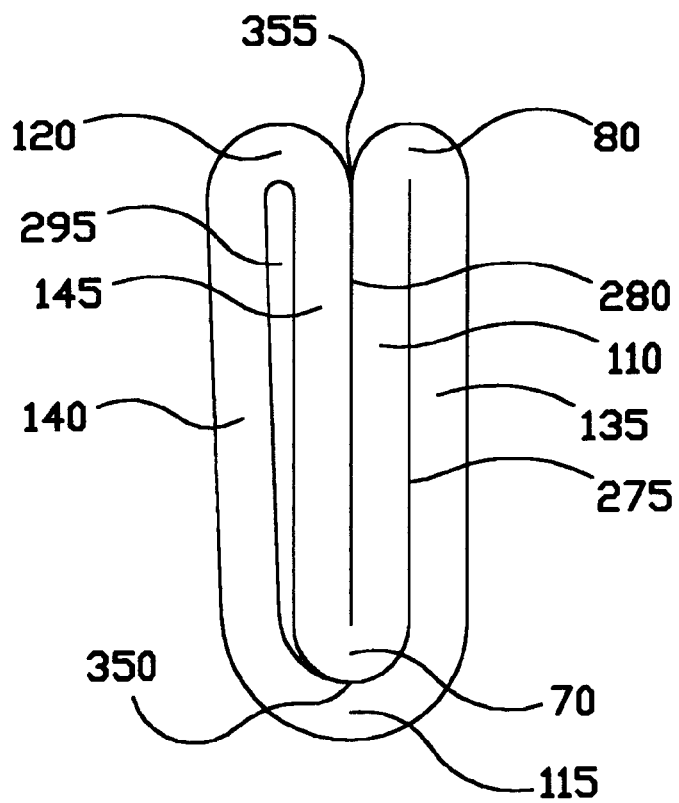
FIG. 6A is a sectional view of the inlet end of the overlap region in a flattened state.

FIG. 6A is a sectional view of the overlap inlet end 255 during the formation of the valve of the present invention. The first 110 and second 135 quadrants are attached by the overlap inlet end first and second quadrant attachment 275. The first 110 and fourth 145 quadrants are attached by the overlap inlet end first and fourth quadrant attachment 280. The third 140 and fourth 145 quadrants form the overlap through-flow member 295. The zero degree wall 70 is attached to the 180 degree wall 115 with an overlap inlet end zero and 180 degree wall attachment 350. The overlap inlet end zero and 180 degree wall attachment 350 extends from the overlap inlet 255 to outlet 260 end forming an overlap zero and 180 degree wall line attachment 340 (see FIG. 5A). The 90 degree wall 80 is attached to the 270 degree wall 120 with an overlap inlet end 90 and 270 degree wall attachment 355. The overlap inlet end 90 and 270 degree wall attachment 355 extends from the overlap inlet 255 to outlet 260 end forming an overlap 90 and 270 degree line attachment 345 (see FIG. 5A). The attachment 275, 280, 350, or 355 can be a wall or surface attachment formed using sutures, staples, adhesives, laser welding, or other attachment means or methods described earlier.

Figure 6B:
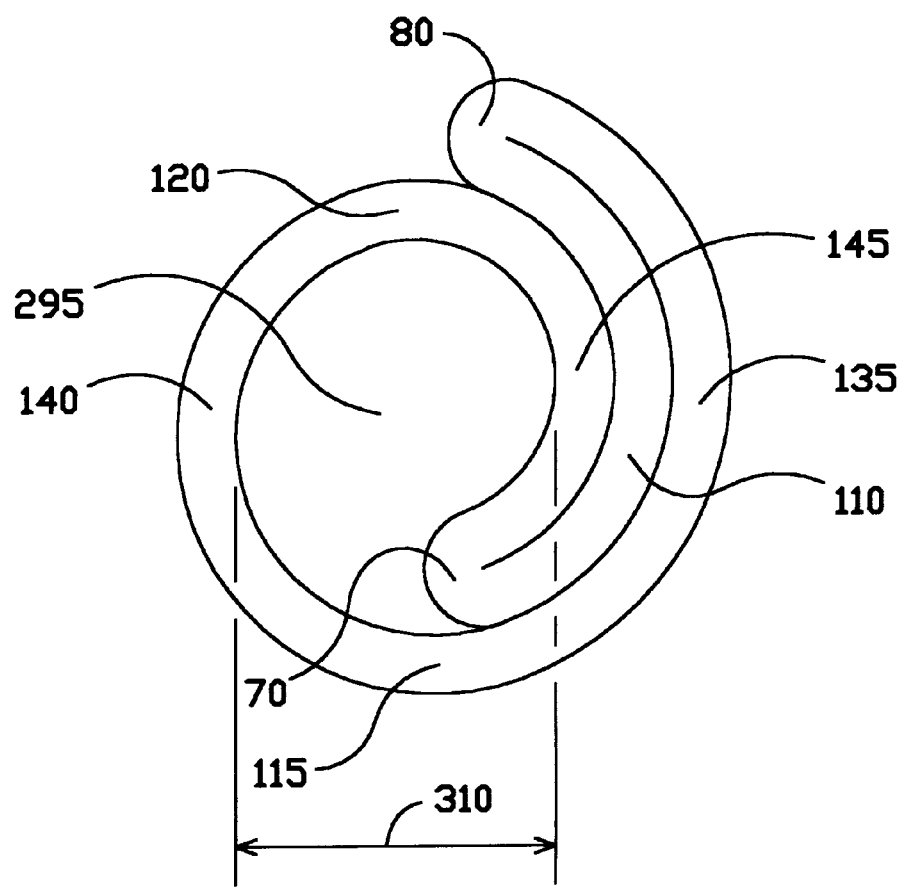
FIG. 6B is a sectional view of the inlet end of the overlap region during antegrade blood flow.

FIG. 6B is a sectional view of the overlap inlet end 255 during blood flow in an antegrade flow direction 100 (see FIG. 5C) through the overlap through-flow member 295. The overlap through-flow member diameter 310 can be approximately one half of the inlet or outlet distended vein segment diameter 22 from which it may be formed. Other configurations can similarly be used to form the overlap inlet end of the present invention. Other reference numerals are the same as those found in FIG. 6A.

Figure 7A:
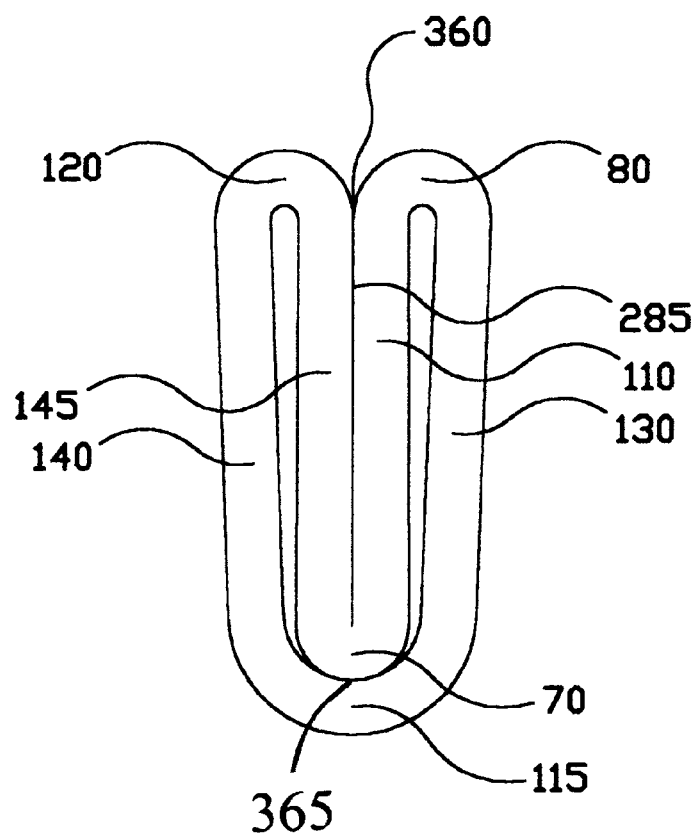
FIG. 7A is a sectional view of the outlet end of the overlap region during venous valve formation.

FIG. 7A is a sectional view of the overlap outlet end 260 during formation. The first 110 and fourth 145 quadrants are attached by the overlap outlet end first and fourth quadrant attachment 285. The 90 degree wall 80 and the 270 degree wall 120 are attached by the overlap outlet end 90 and 270 degree wall attachment 360. The zero degree wall 70 is attached to the 180 degree wall 115 at the overlap outlet end 260 by an overlap outlet end zero and 180 degree wall attachment 365. The first 110 and fourth 145 quadrants are attached by the overlap outlet end first and fourth quadrant attachment 285. The first quadrant 10 is not attached to the second quadrant 135 and the third quadrant 140 is not attached to the fourth quadrant 145 at the overlap outlet end. Surface or wall attachments are formed using materials and methods as described earlier.

Figure 7B:
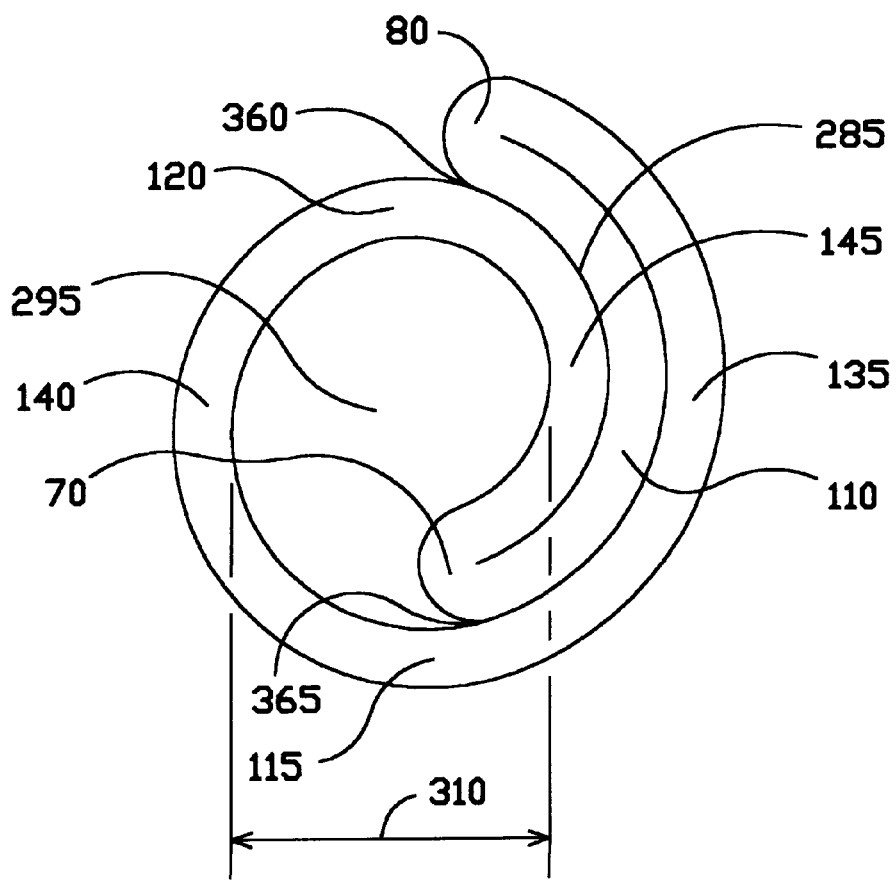
FIG. 7B is a sectional view of the outlet end of the overlap region during antegrade blood flow.

FIG. 7B is a sectional view of the overlap outlet end with blood flow in an antegrade flow direction 100 (see FIG. 5C) showing the overlap through-flow member 295 with an overlap through-flow member diameter 310. All reference numerals are the same as found in FIG. 7A.

Figure 7C:
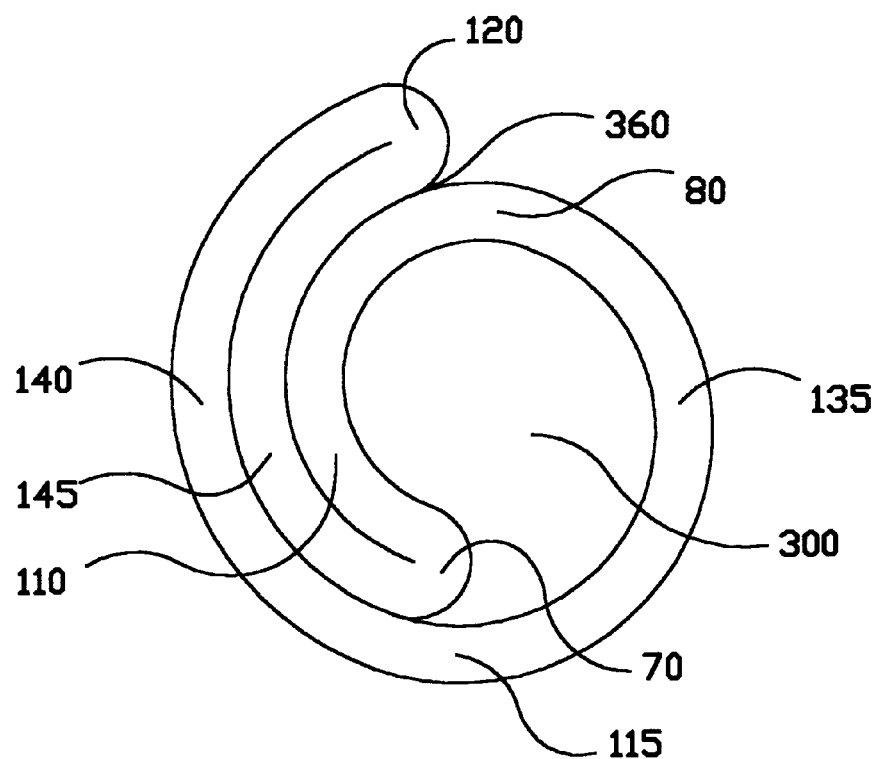
FIG. 7C is a sectional view of the outlet end of the overlap region during retrograde blood flow.

FIG. 7C is a sectional view of the overlap outlet end with retrograde filling of the overlap sinus member 300. Retrograde filling of the overlap sinus member 300 causes retrograde flow through the through-flow member 295 to reduce significantly or cease. All other reference numerals are the same as in FIG. 7A.

As seen in FIGS. 5A and 5C, the venous valve 210 of the present invention can have an inlet 215 or an outlet 225 transition region to provide a smooth transition of blood flow from the inlet distended vein 230 or the outlet distended vein 235 to the overlap region 220. The inlet 215 or outlet 225 transition region can be contiguous with the overlap region 220 or the transition regions can be contiguous with the inlet 230 or outlet 235 distended veins; or the inlet 215 or outlet 225 transition regions can be attached to the overlap region 220, or the transition regions can be attached to the inlet 230 or outlet 235 distended veins using sutures or other attachment means.

Figure 8A:
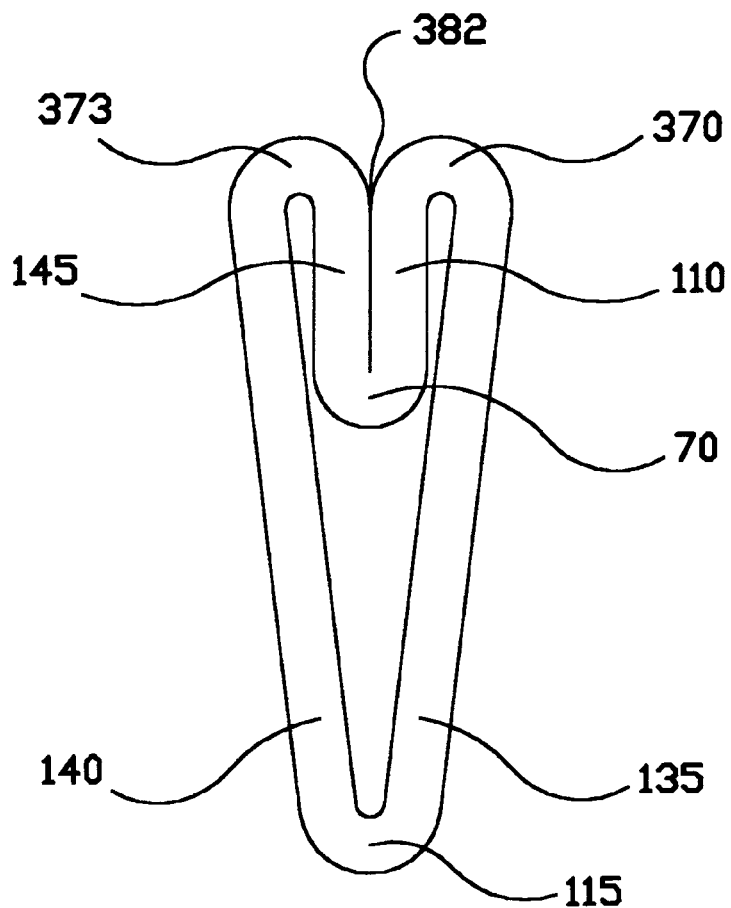
FIG. 8A is a sectional view of one inlet transition region embodiment near the overlap region during venous valve formation.
Figure 8B:
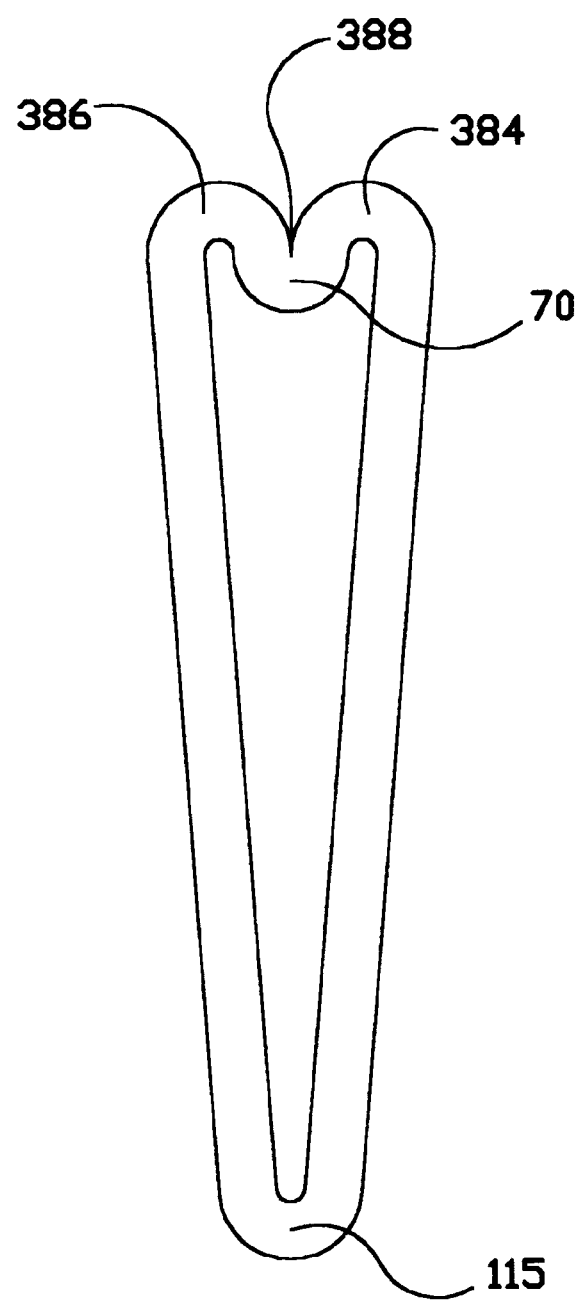
FIG. 8B is a sectional view of one inlet transition region embodiment near the inlet distended vein during venous valve formation.

FIGS. 8A and 8B are sectioned views of the inlet transition region 215 without blood flow and in a state of being formed. The zero degree wall 70 and the 180 degree wall 115 are shown for reference. As shown in FIG. 8A approximately a 45 degree wall 370 can be attached to approximately the 315 degree wall 373 at an inlet transition 45 and 315 degree wall attachment 382. As shown in FIG. 8B approximately the 20 degree wall 384 can be attached to approximately a 340 degree wall 386 at an inlet transition 20 and 340 degree wall attachment 388. Additional inlet transition attachments are made in a similar manner to form a line of inlet transition wall attachments between the first 110 and fourth 145 quadrants that form a tapered line of attachments in the inlet transition region 215 from the overlap region 220 to the inlet distended vein 230 (see FIGS. 5A and 5B). This tapered line of attachment forms a beveled attachment that extends from the overlap region to the distended vein with either a straight or curved bevel that directs the blood flow smoothly from the inlet distended vein 230 to the overlap region 220. All reference numerals correspond to those elements previously or otherwise described.

Figure 8C:
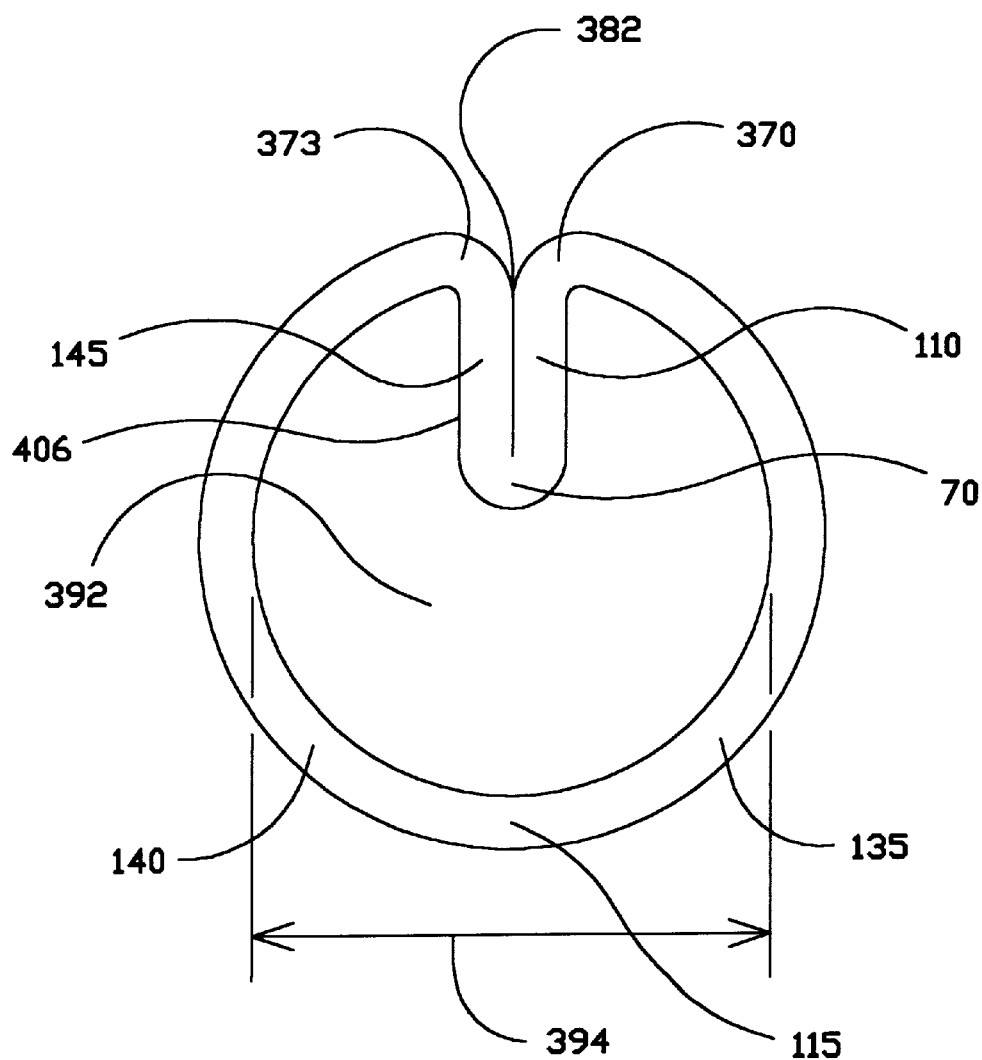
FIG. 8C is a sectional view of one inlet transition region embodiment near the overlap region during antegrade blood flow.
Figure 8D:
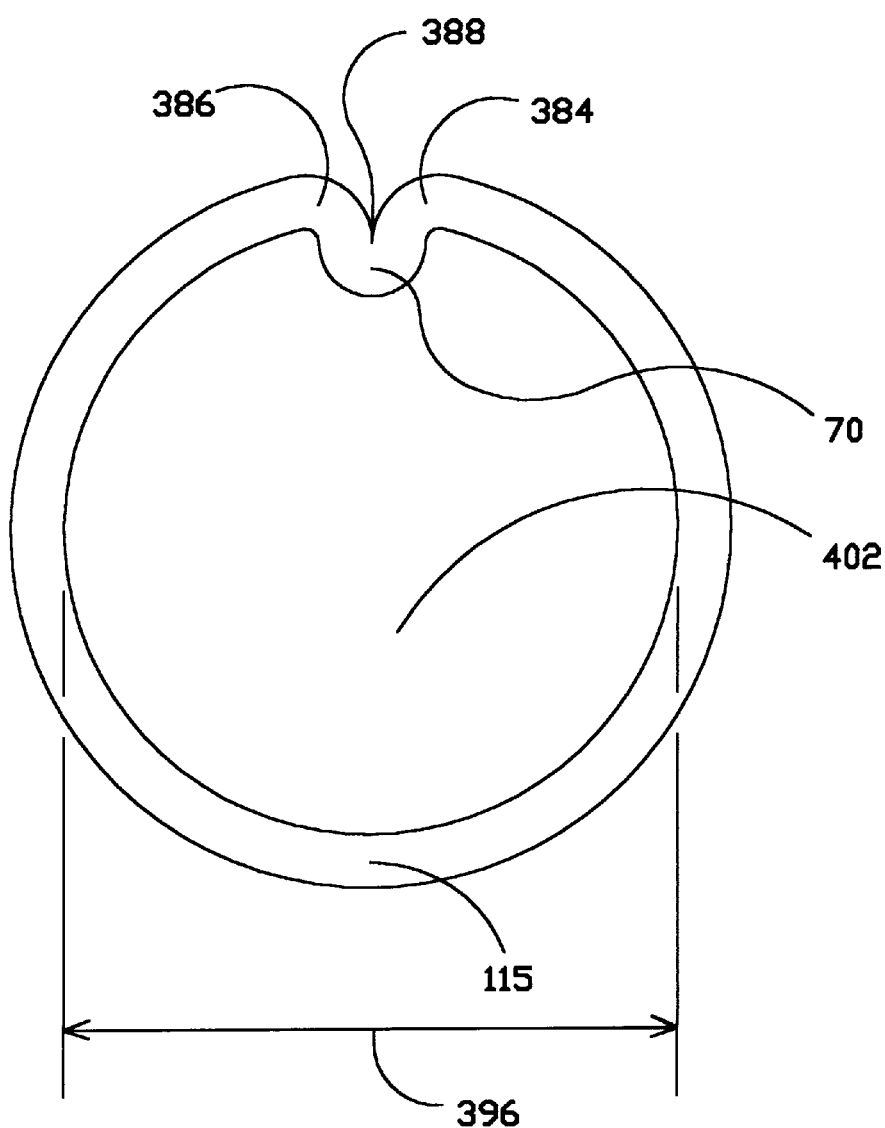
FIG. 8D is a sectional view of one inlet transition region embodiment near the inlet distended vein during antegrade blood flow.

FIGS. 8C and 8D are similar to FIGS. 8A and 8B except that the inlet transition region 215 is shown as though blood flow in an antegrade flow direction 100 were present in an inlet transition flow lumen 392. An inlet transition diameter 394 for the inlet transition flow lumen 392 of FIG. 8C is smaller than an inlet transition diameter 396 for an inlet transition flow lumen 402 of FIG. 8D. Inlet transition excess tissue 406 is shown extending into the inlet transition flow lumen 392 of FIG. 8C. The inlet transition excess tissue can be attached to the first or fourth quadrant wall or it can be trimmed off and removed. All reference numerals correspond to those elements previously or otherwise described.

Figure 9A:
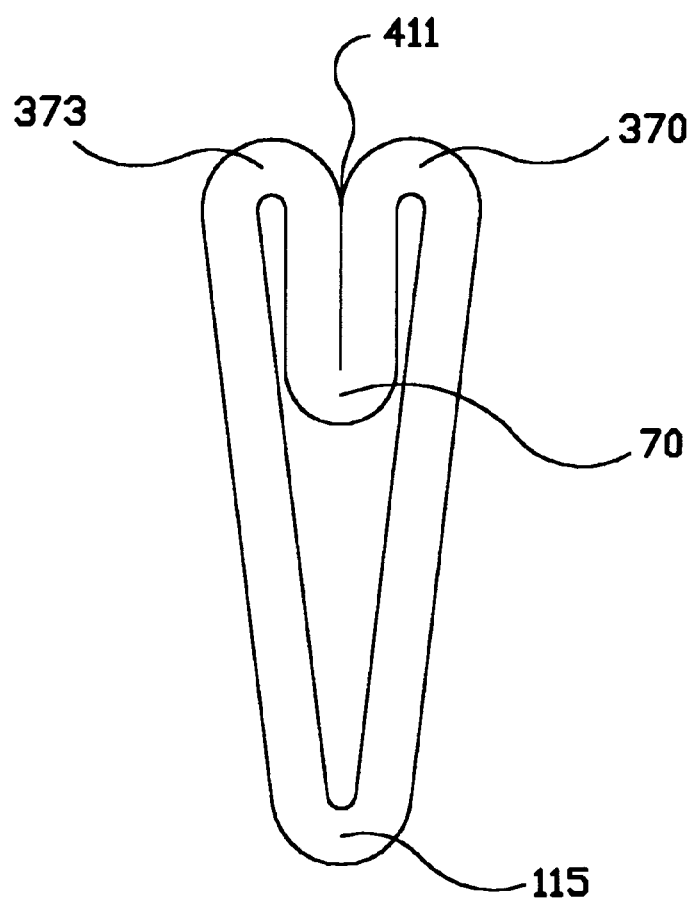
FIG. 9A is a sectional view of one outlet transition region embodiment near the overlap region during venous valve formation.
Figure 9B:
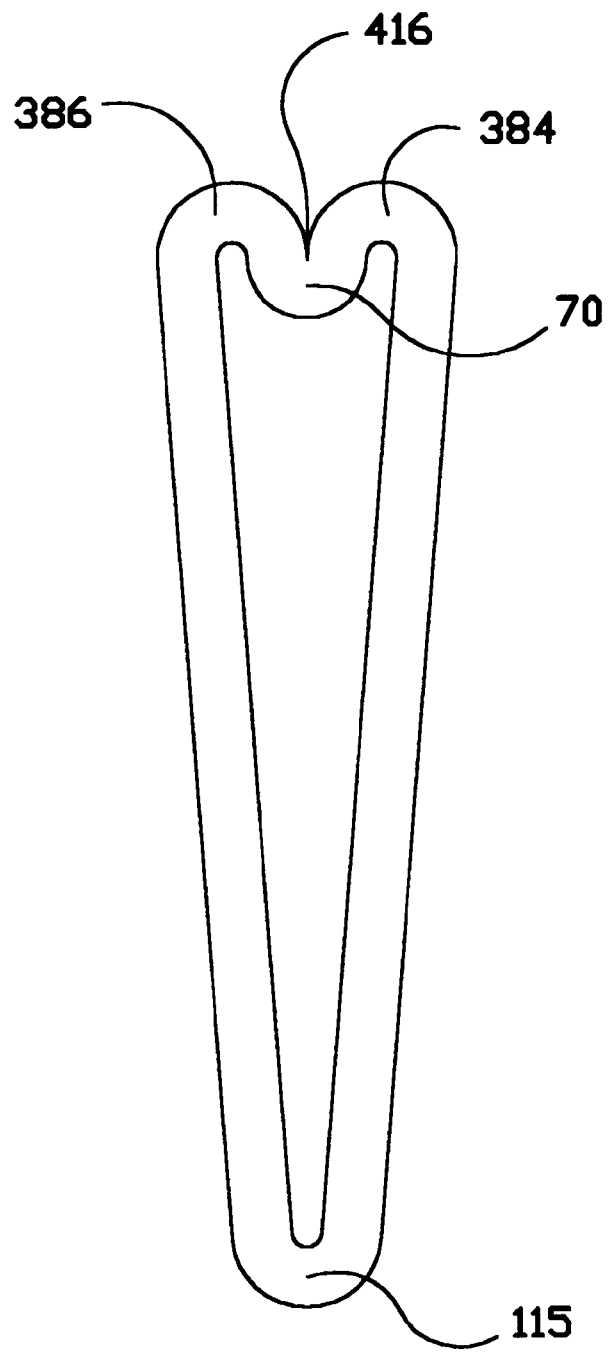
FIG. 9B is a sectional view of one outlet transition region embodiment near the inlet distended vein during venous valve formation.

One embodiment for forming the outlet transition region 225 is shown in FIGS. 9A and 9B. FIGS. 9A and 9B are sectioned views of the outlet transition region 225 without blood flow and in a state of being formed. The zero degree wall 70 and the 180 degree wall 115 are shown for reference. As shown in FIG. 9A approximately the 45 degree wall 370 can be attached to approximately the 315 degree wall 373 at an outlet transition 45 and 315 degree wall attachment 411. As shown in FIG. 9B approximately the 20 degree wall 384 can be attached to approximately the 340 degree wall 386 at the outlet transition 20 and 340 degree wall attachment 416. Additional outlet transition attachments are made in a manner similar to that described for the inlet transition region 215 to form a continuous line of outlet transition wall attachments that form a tapered transition from the overlap region 220 to the outlet distended vein 235. This tapered line of attachment forms a beveled attachment that extends from the overlap region to the distended vein with either a straight or curved bevel that directs the blood flow smoothly from the overlap region 220 to the outlet distended vein 230. Wall and surface attachments are formed using materials and methods as discussed earlier.

Figure 9C:
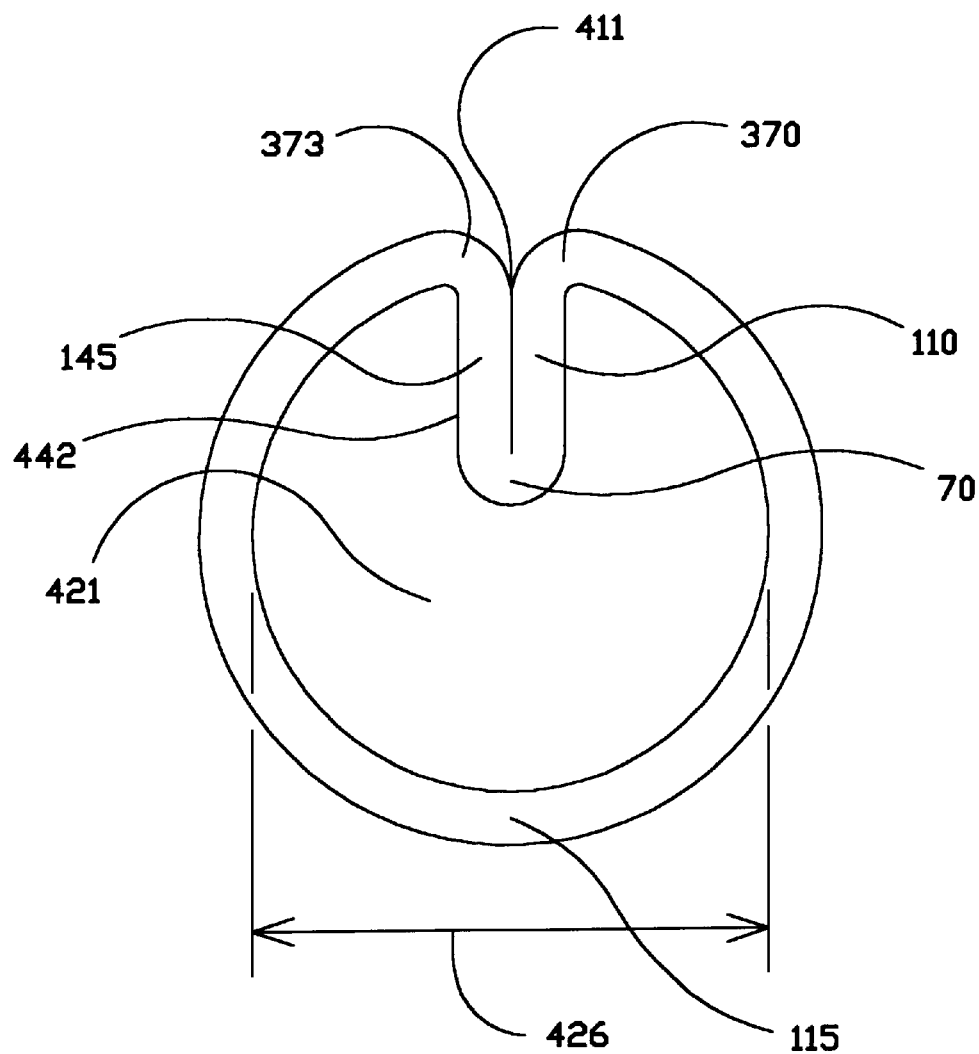
FIG. 9C is a sectional view of one outlet transition region embodiment near the overlap region during antegrade blood flow.
Figure 9D:
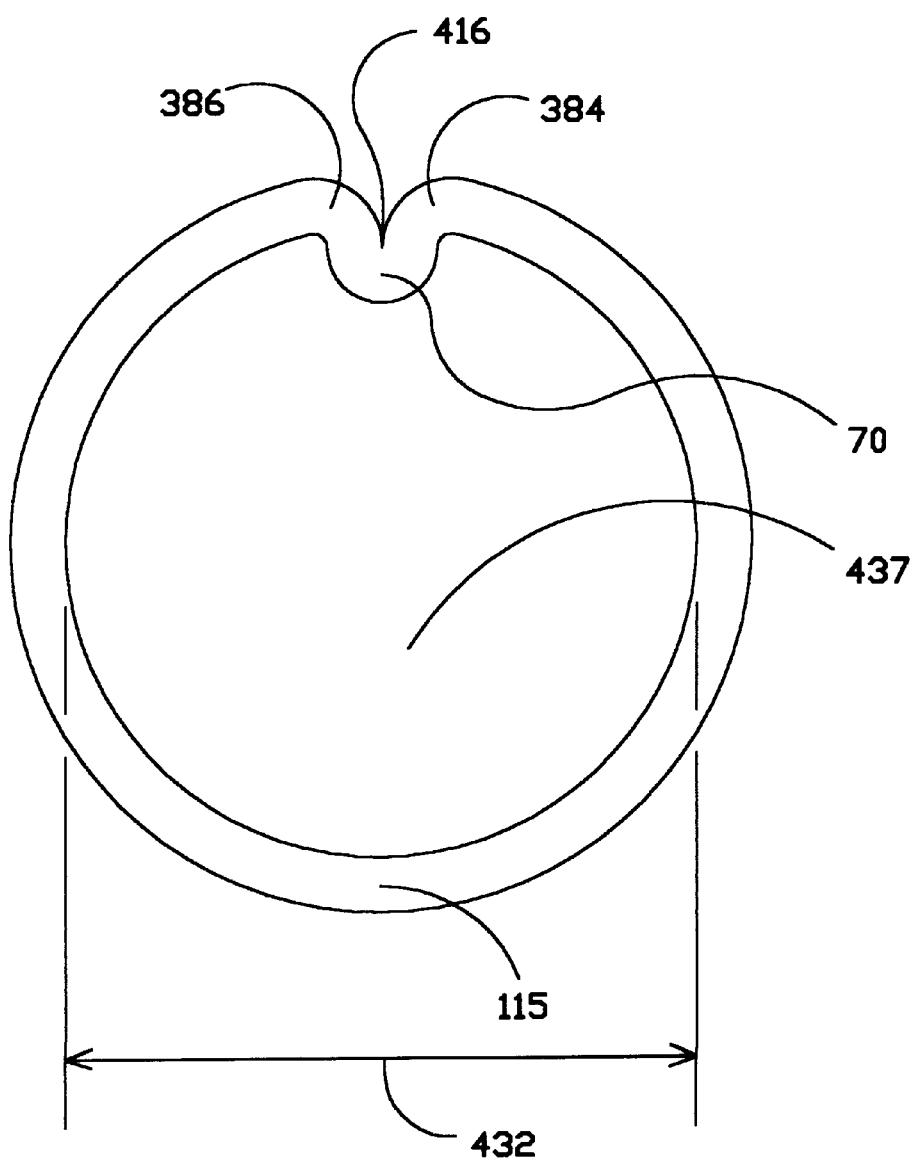
FIG. 9D is a sectional view of one outlet transition region embodiment near the inlet distended vein during antegrade blood flow.

FIGS. 9C and 9D are similar to FIGS. 9A and 9B except that the outlet transition region 225 is shown as though blood flow in an antegrade flow direction 100 were present in an outlet transition flow lumen 421. An outlet transition diameter 426 for the outlet transition flow lumen 421 of FIG. 9C is smaller that an outlet transition diameter 432 for an outlet transition flow lumen 437 of FIG. 9D. Outlet transition excess tissue 442 is shown extending into the outlet transition flow lumen 421 of FIG. 9C. The outlet transition excess tissue 442 can be attached to the first 110 or fourth 145 quadrant wall or it can be trimmed off and removed. All reference numerals correspond to those elements previously or otherwise described.

Figure 10A:
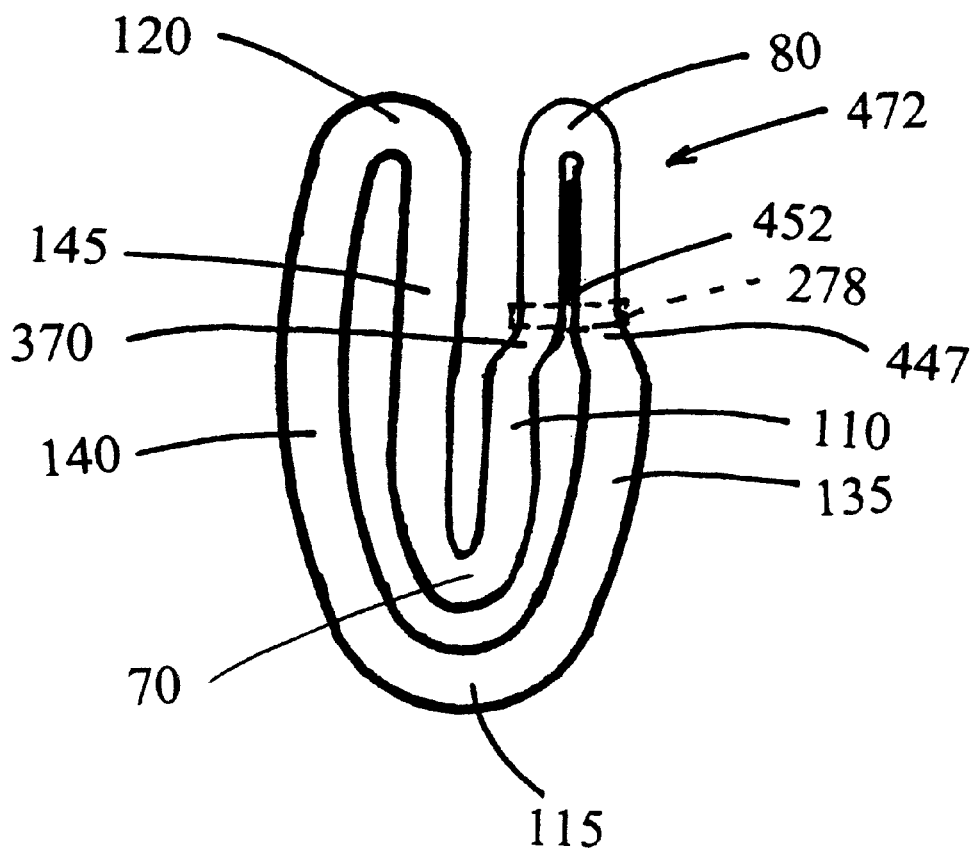
FIG. 10A is a sectional view of a second inlet transition region embodiment near the overlap region during venous valve formation.
Figure 10B:
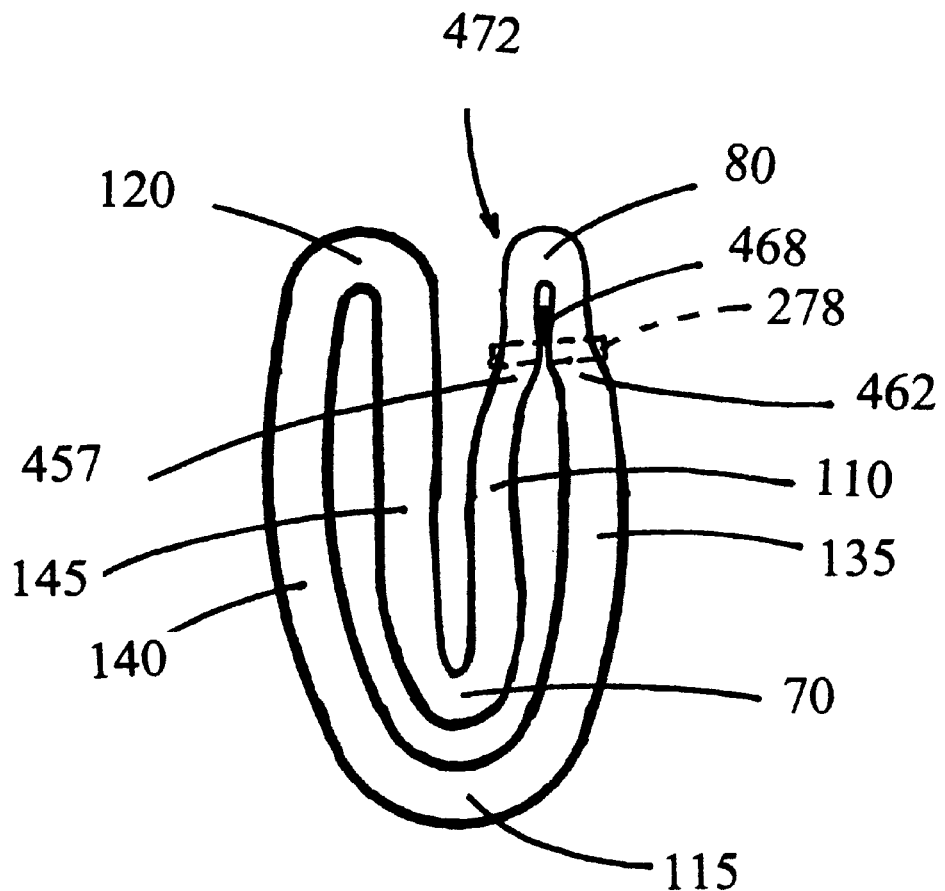
FIG. 10B is a sectional view of a second inlet transition region embodiment near the outlet distended vein during venous valve formation.

One embodiment for forming the inlet transition region 215 is shown in sectional views in FIGS. 10A and 10B. FIG. 10A represents a position along the inlet transition region similar to that of FIG. 8A and FIG. 10B represents a position similar to that of FIG. 8B. In FIGS. 10A and 10B it is understood that the inlet transition region 215 is shown in a flat conformation such that it may not have blood flow going through it such as during the formation of the venous valve 210 of the present invention. FIGS. 10A and 10B show the first 110, second 135, third 140, and fourth 145 quadrants in a similar conformation to that found in the overlap region 220 for ease of understanding the formation of the transition region of this embodiment of the present invention. In FIGS. 10A and 10B the zero degree wall 70 and the 180 degree wall 115 are not attached, and the 90 degree wall 80 and the 270 degree wall 120 are not attached. In FIG. 10A attachment of the first quadrant 110 to the second quadrant 135 can occur approximately from a 45 degree wall 370 to a 135 degree wall 447 forming an inlet transition 45 and 135 degree wall attachment 452. An example of an attachment means 278 is shown in FIG. 10A, and can include sutures or other materials or attachment methods or attachment means as described earlier. In FIG. 10B attachment of the first quadrant 110 to the second quadrant 135 can occur approximately from a 70 degree wall 457 to a 110 degree wall 462 forming an inlet transition 70 and 110 degree wall attachment 468. FIGS. 10A and 10B represent two sections along the inlet transition region 215; the locations for attachment of portions of the first 110 and second 135 quadrants are approximate and correspond to positions along the axial length of the transition region similar to those found in FIGS. 8A and 8B, respectively. A continuous or intermittent line of attachments is intended to form a tapered transition for blood flow from the inlet distended vein 230 to the overlap inlet end 255 to direct blood flow from the inlet distended vein 230 into the overlap inlet end 255. It is understood that additional attachments are made along the entire inlet transition region 215 extending from the overlap region 220 to the inlet distended vein 230. Inlet transition excess tissue 472 can be trimmed off or removed provided that the attachments made from the first 110 to the second 135 quadrants form a continuous beveled line from the overlap region 220 to the inlet distended vein 230 that can withstand venous blood pressure without leakage. All reference numerals correspond to those elements previously or otherwise described.

Figure 10C:
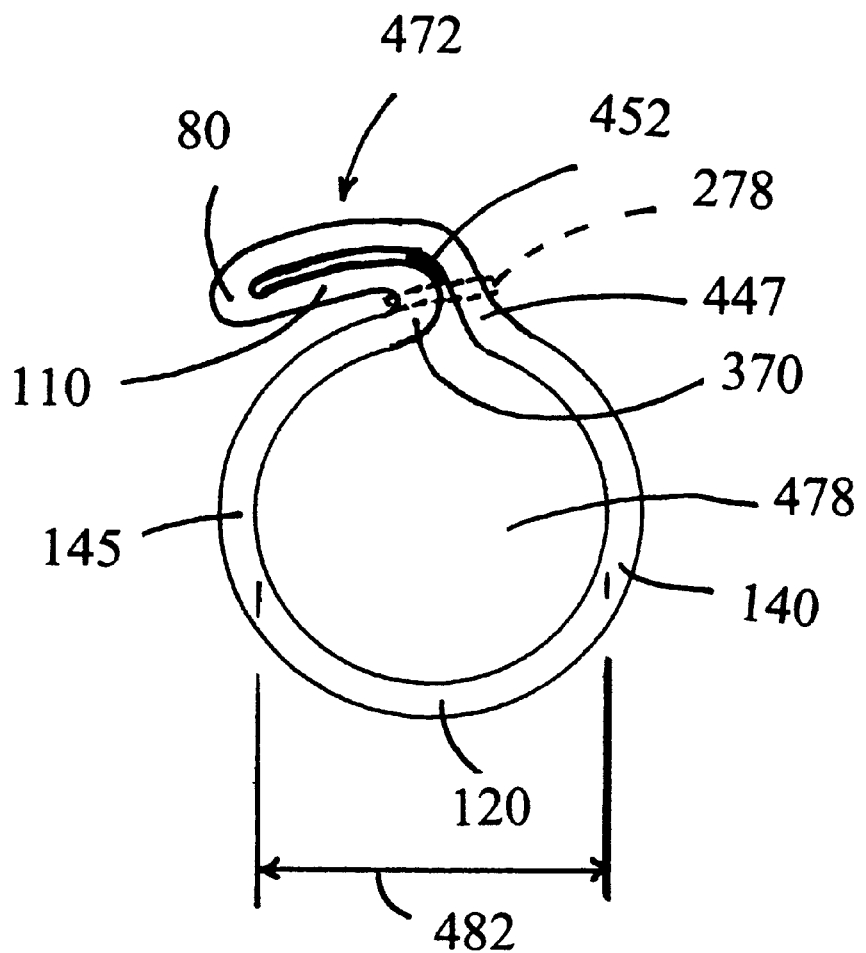
FIG. 10C is a sectional view of a second inlet transition region embodiment near the overlap region during antegrade blood flow.
Figure 10D:
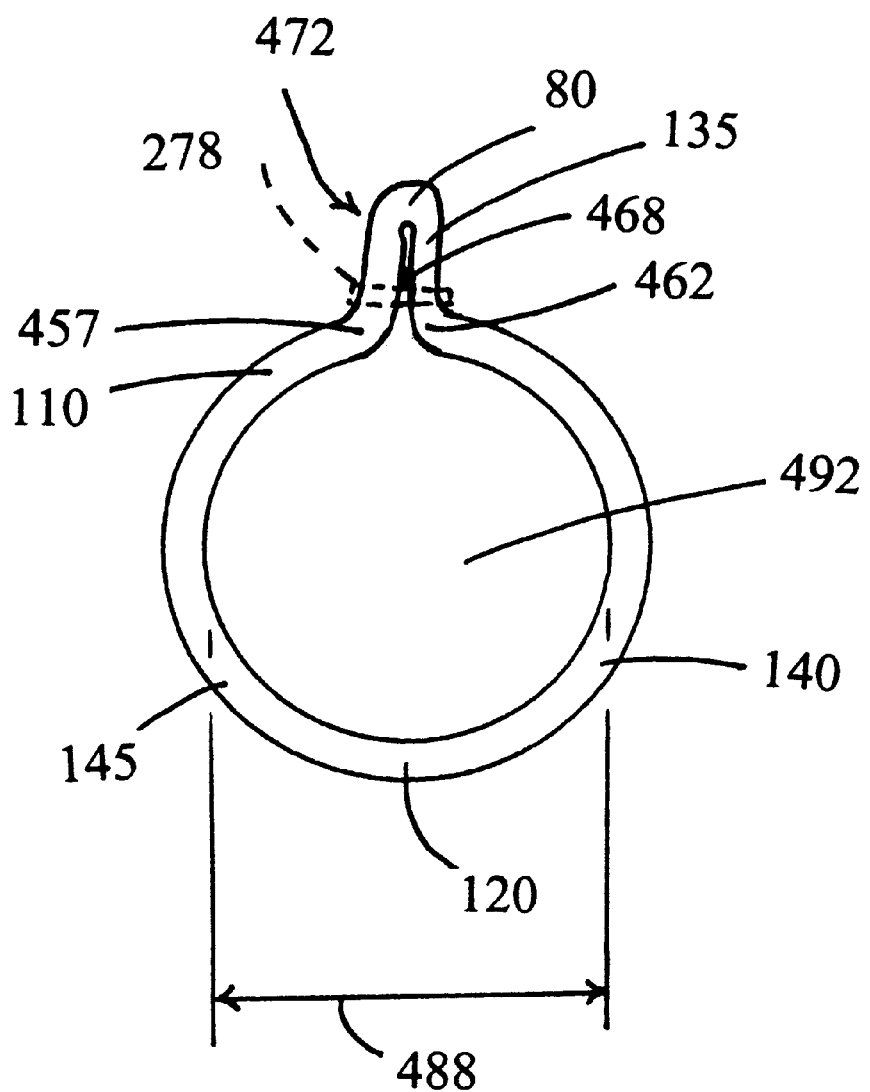
FIG. 10D is a sectional view of a second inlet transition region embodiment near the outlet distended vein during antegrade blood flow.

FIGS. 10C and 10D are similar to those of FIGS. 10A and 10B respectively except that the inlet transition region 215 is shown as though blood flow with an antegrade flow direction 100 (see FIG. 5C) were passing through an inlet transition flow lumen 478 of FIG. 10C. The inlet transition flow lumen 478 shown in FIG. 10C has an inlet transition diameter 482 that is smaller than the inlet transition diameter 488 of the inlet transition flow lumen 492 shown in FIG. 10D. The inlet transition diameter of the inlet transition flow lumen gets progressively smaller as it extends from the inlet distended vein 230 to the overlap region 220. The inlet transition excess tissue 472 does not extend into the inlet transition lumen of this embodiment and can be cut off without affecting the function of the present invention. All other reference numerals are the same as those in FIGS. 10A and 10B.

Figure 11A:
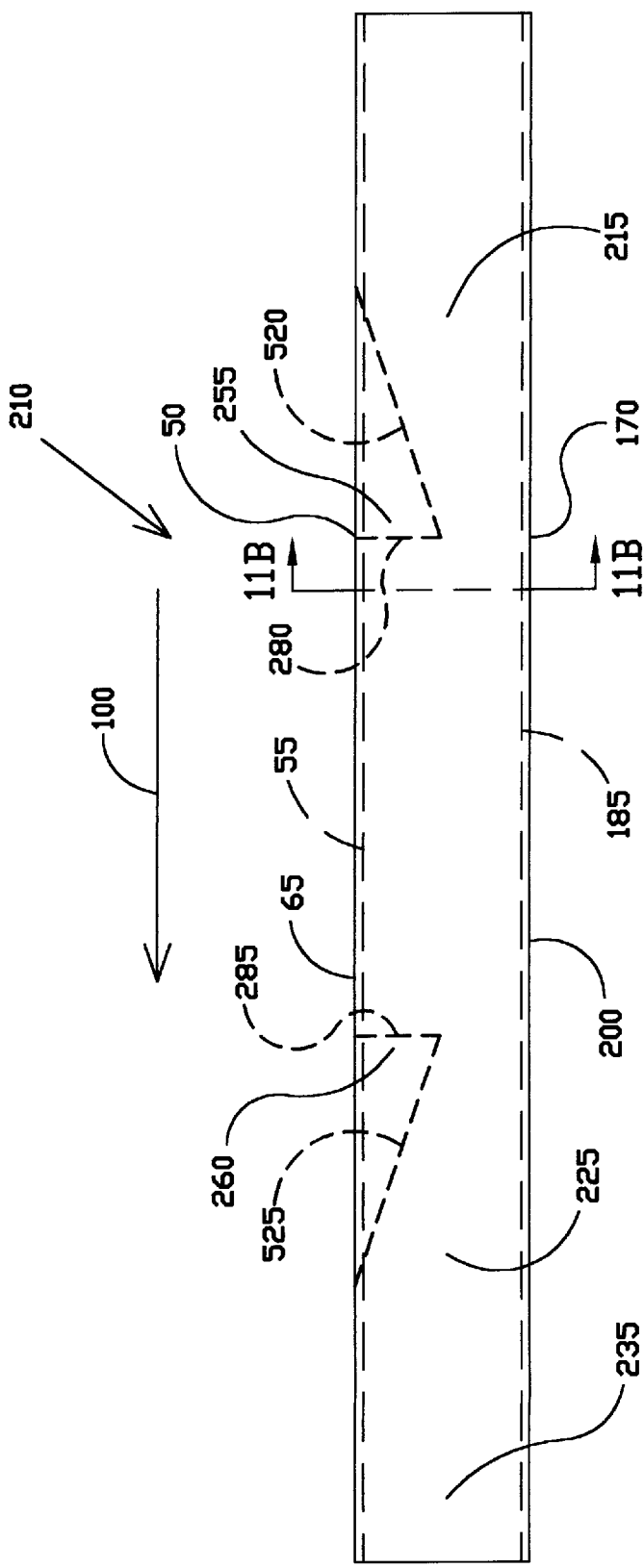
FIG. 11A is a partially sectioned view of an alternate embodiment of the venous valve of this invention in an early stage of formation with early attachment lines.
Figure 11B:
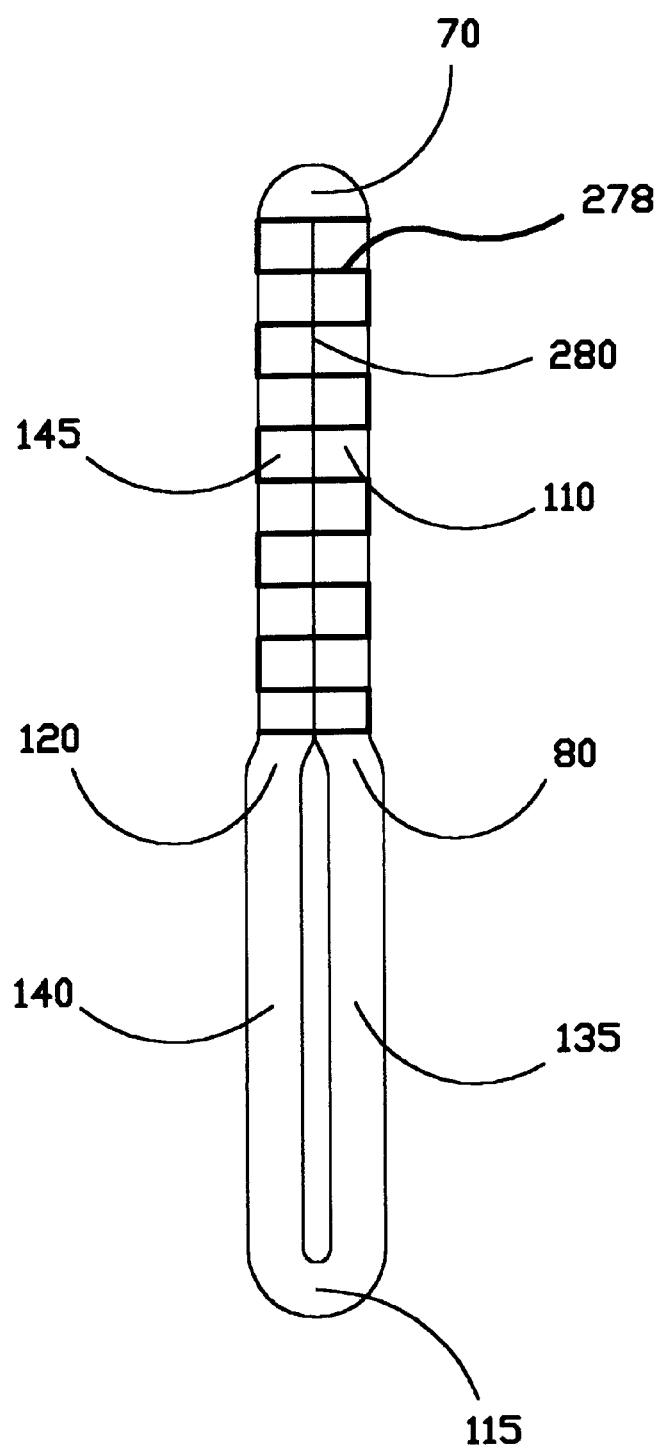
FIG. 11B is a sectional view of the inlet end of the overlap region during an early stage or formation.

FIGS. 11A–D describe an alternate embodiment of the present invention. FIGS. 11A and 11B show a distended vein segment 5 lying flat with the fourth 145 quadrant and third 140 quadrant lying adjacent to the first 110 and second 135 quadrant, respectively. The overlap region 220 extends from the overlap inlet end 255 to the overlap outlet end 260. The inlet transition region 215 can be contiguous with or it can be attached to the overlap inlet end 255 and the outlet transition region 225 can be contiguous with or it can be attached to the overlap outlet end 260. The inlet distended vein 230 can be contiguous with or it can be attached to the inlet transition region 215 and the outlet distended vein 235 can be contiguous with or it can be attached to the outlet transition region 225. The outer surface zero degree line 65 and zero degree wall 70 and the inner surface zero degree line 55 are shown near the top of FIGS. 11A and 11B, and the outer surface 180 degree line 200 and 180 degree wall and inner surface 180 degree line 185 are shown near the bottom of FIGS. 11A and 11B. An overlap inlet end first and fourth quadrant attachment 280 is formed to attach the first quadrant 110 to the fourth quadrant 145 at the overlap inlet end 255. This overlap inlet end first and fourth quadrant attachment 280 can be made using suture, staples, adhesives, tissue bonding agents, fusion methods, metallic fiber, polymeric fiber, or other surface or wall attachment means. An example of such wall or surface attachment means is shown by reference numeral 278 in FIG. 11B, it can be formed of suture or other material as described earlier for previous embodiments. An overlap outlet end first and fourth quadrant attachment 285 is formed to attach the first quadrant 110 to the fourth quadrant 145 at the overlap outlet end 260 using surface or wall attachment means. The overlap inlet end and outlet end first and fourth quadrant attachments 280 and 285 form the valve cusp attachment. It is understood that such valve cusp attachment requires only that a portion of the first 110 and fourth 145 quadrant walls area 21 be attached together.

Figure 11C:
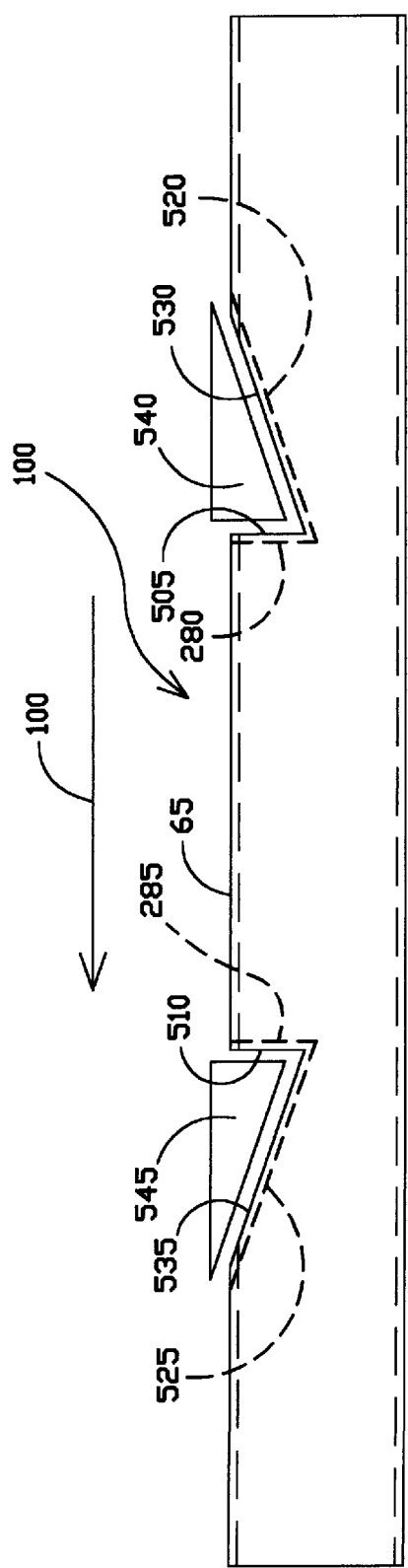
FIG. 11C is a partially sectioned view of an alternate embodiment of the venous valve of this invention in an early stage of formation with overlap region and transition region cuts.

The vein walls 20 of the first 110 and fourth 145 quadrants are cut adjacent to the overlap inlet end first and fourth quadrant attachment 280 at an overlap inlet cut 505 as shown in FIG. 11C. Similarly, the vein walls 20 of the first 110 and fourth 145 quadrants are cut adjacent to the overlap outlet end first and fourth quadrant attachment 285 at an overlap outlet cut 510 as shown in FIG. 11C.

Figure 11D:
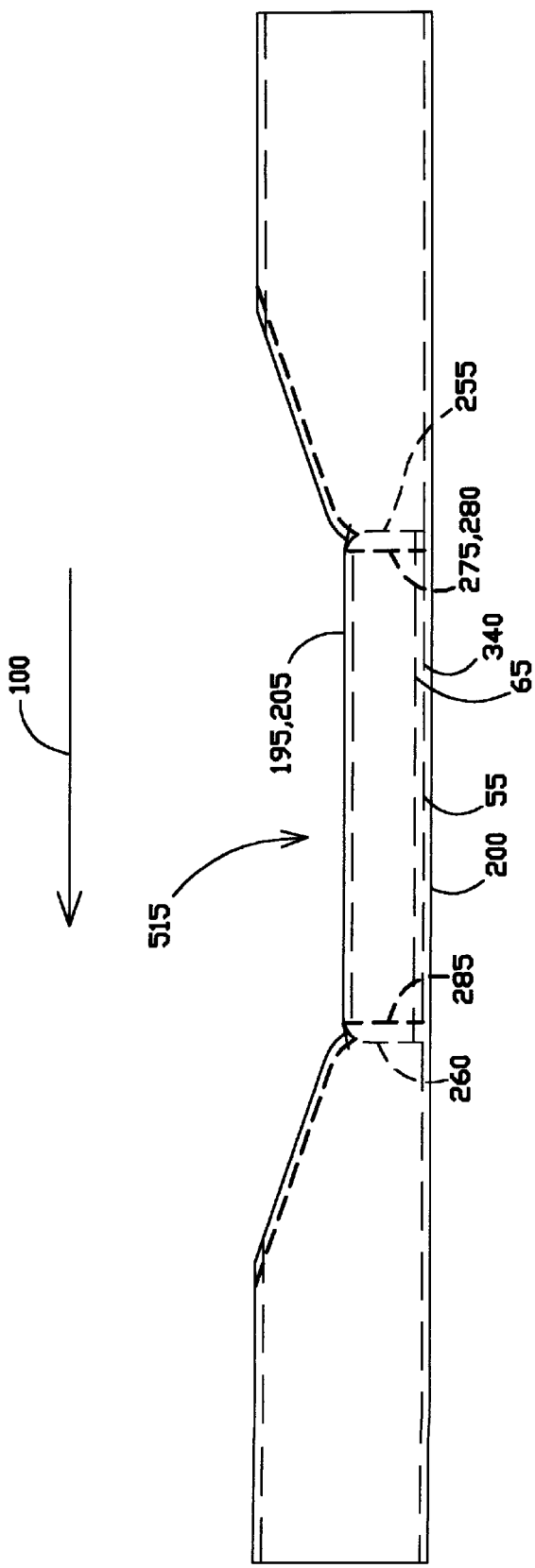
FIG. 11D is a partially sectioned view of an alternate embodiment of the venous valve of this invention in an early stage of formation with an inverted fold.

The first 110 and fourth 145 quadrants of the overlap region 220 undergo an inverted fold 515 to bring the inner surface zero degree line 55 into direct contact with the inner surface 180 degree line 185 in the overlap region 220 as shown in FIG. 11D. The zero degree wall line 75 is attached to the 180 degree wall line 125 at the overlap zero and 180 degree wall line attachment 340 forming a divisional attachment in the overlap region 220 using sutures, staples, bonding agents, fusion methods or other surface or wall attachment means. This divisional attachment forms two separate lumens or spaces that do not have significant leakage between them. It is understood that the overlap zero and 180 degree wall line attachment 340 need not be attached from the overlap inlet 255 to outlet 260 end as long as two tubular members are formed by a divisional attachment, a divisional attachment being a surface or wall attachment that can form two separate flow channels that do not allow substantial blood flow to pass across the attachment.

Figure 11E:
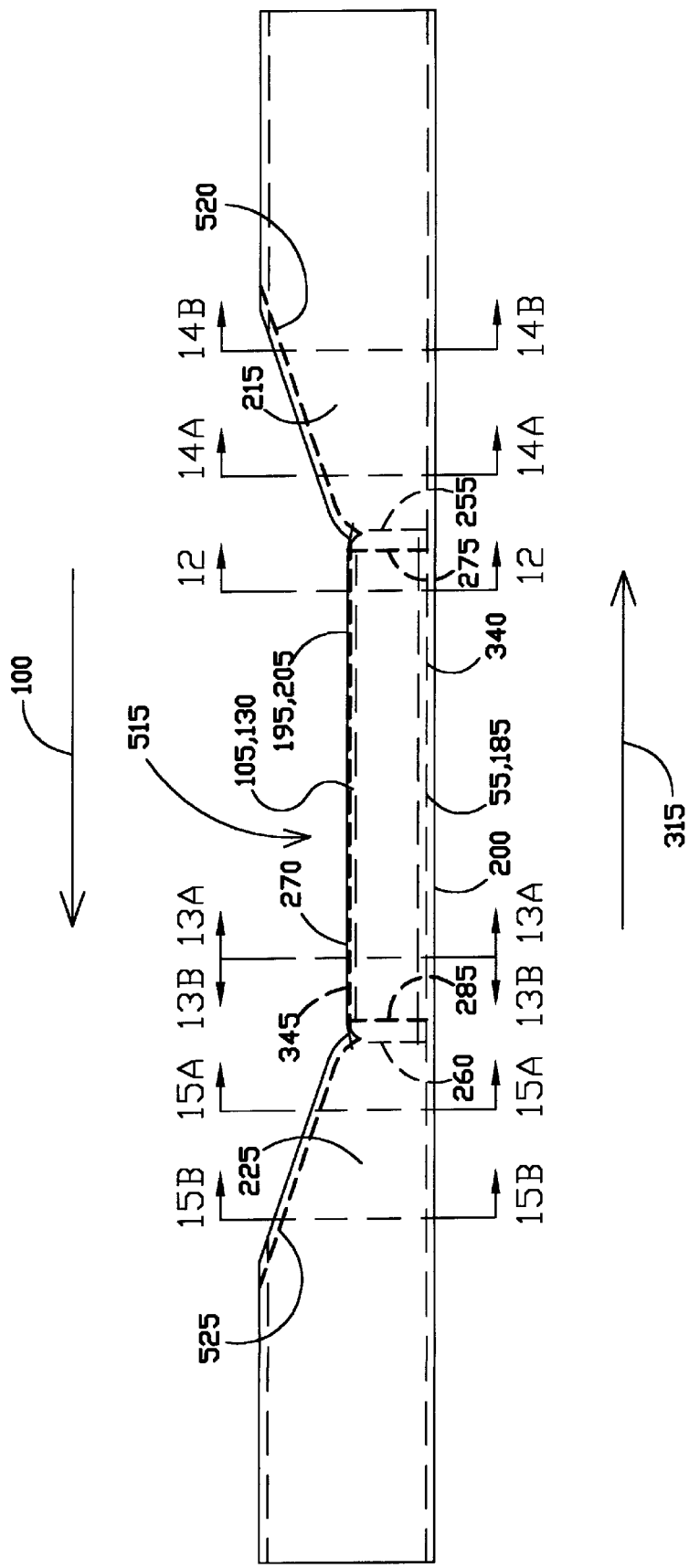
FIG. 11E is a partially sectioned view of an alternate embodiment of the venous valve of this invention.

At the overlap inlet end 255, the first 110 and second 135 quadrants are attached forming an overlap inlet end first and second quadrant attachment 275 or closure attachment as shown in FIGS. 11D and 11E. The closure attachment does not allow antegrade blood flow to enter between the first 110 and second 135 quadrants. In the overlap region 220 the outer surface 90 degree line 195 is attached to the outer surface 270 degree line 205 forming the outer surface 90 and 270 degree line attachment 270 or approximation attachment; this attachment can be found along only a portion of the outer surface 90 and 270 degree line attachment 270 without affecting the function of the vein valve 210 of the present invention. The approximation attachment serves to hold the 90 and 270 degree lines in approximation with each other at least intermittently. The 90 degree wall line 105 and the 270 degree wall line 130 are attached in the overlap region 220 to form the overlap 90 and 270 degree wall line attachment 345. At this stage of formation, the overlap region 220 has been formed into one embodiment of the venous valve 210 of this invention. An inlet 215 or outlet 225 transition region can be contiguous with or attached to the overlap region 220. The overlap region 220 could also be interpositionally attached between an inlet 230 or outlet 235 distended vein. The overlap outlet end first and fourth quadrant attachment 285 forms a valve cusp free edge or commissure as described in other previous embodiments of the invention. The inverted fold 515 of the first 110 and fourth 145 quadrants provides the valve cusp free edge of this embodiment that has the endothelialized surface folded over such that it approximates the other endothelialized surface. The endothelialized surface of the commissure is similar to the inner surface of the distended vein. The venous valve of FIG. 11E is shown in a conformation that would provide for antegrade or retrograde blood flow. All reference numerals correspond to those elements previously or otherwise described.

Figure 12:
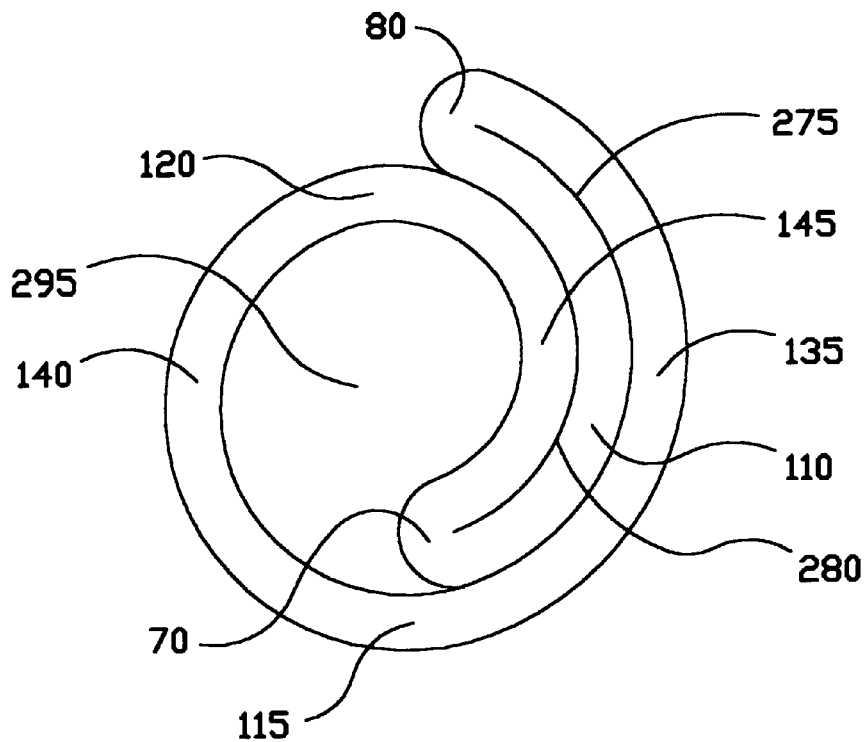
FIG. 12 is a sectional view of an inlet end of an overlap region of an alternate embodiment of the venous valve of this invention with antegrade blood flow.

FIG. 12 is a sectional view at the overlap inlet end 255 showing the overlap inlet end first and fourth quadrant attachment 280 and the overlap inlet end first and second quadrant attachment 275. The overlap inlet end first and second quadrant attachment 275 forms a closure attachment that will prevent blood flow in an antegrade direction 100 (see FIG. 11E) from entering between the first 110 and second 135 quadrants. The overlap through-flow member 295 formed by the third 140 and fourth 145 quadrants provides space for antegrade blood flow through the overlap region 220 (FIG. 11E).

Figure 13A:
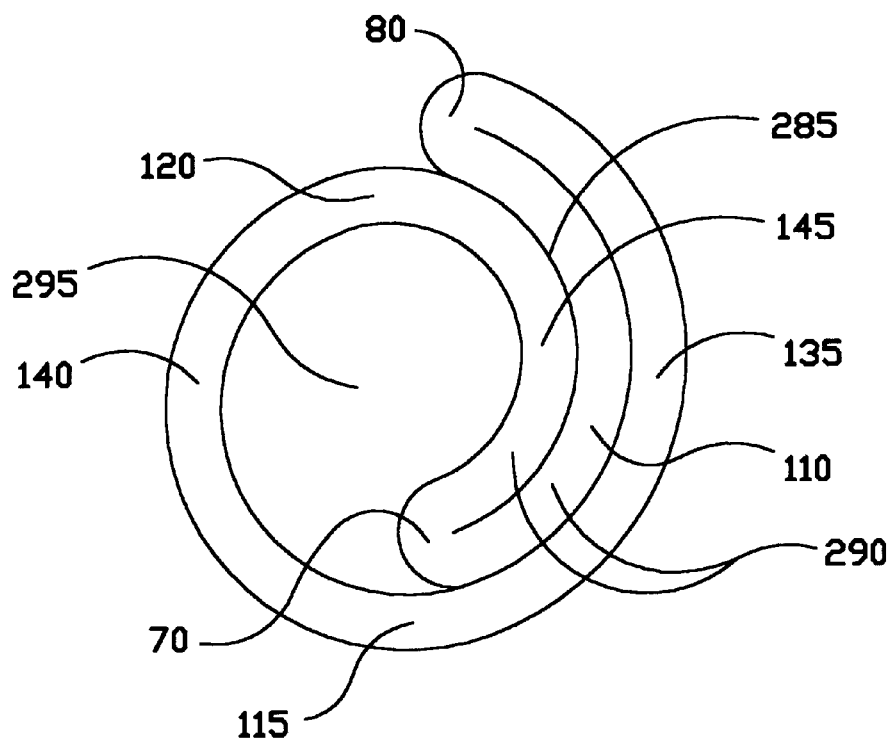
FIG. 13A is a sectional view of an outlet end of an overlap region of an alternate embodiment of the venous valve of this invention with antegrade blood flow.
Figure 13B:
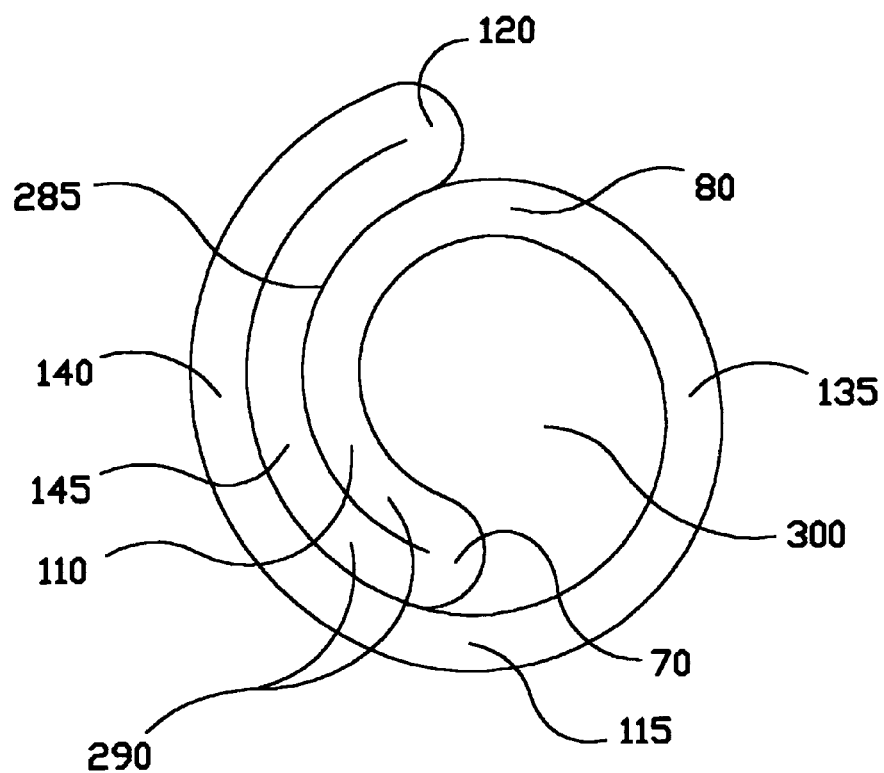
FIG. 13B is a sectional view of an outlet end of an overlap region of an alternate embodiment of the venous valve of this invention with retrograde blood flow into an overlap sinus member.

FIGS. 13A and 13B are sectional views of the overlap outlet end showing the overlap outlet end first and fourth quadrant attachment 285. In FIG. 13A the overlap through-flow member 295 provides space for blood flow in an antegrade direction 100; the valve cusp 290 which is formed from the first 110 and fourth 145 quadrants, is in contact with the second quadrant 135. During the initiation of retrograde flow, the valve cusp 290 moves into contact with the third quadrant 140 as shown in FIG. 13B. Blood will flow into the overlap sinus member 300 causing the valve cusp 290 to prevent continued blood flow in a retrograde direction 315 (see FIG. 11E) in the overlap through-flow member 295 as the valve cusp remains in contact with the third quadrant 140. It is understood that the valve cusp 290 is formed by an attachment of a portion of the first quadrant 110 to a portion of the fourth quadrant 145 along a wall line attachment. This attachment could be formed by attaching a portion of a wall area 21 of the first quadrant 110 to a portion of a wall area 21 of the fourth quadrant 145. Such a valve cusp 290 could similarly be formed by attachment of two sectors together forming a wall line attachment or a wall area attachment.

The inlet 215 and outlet 225 transition regions can be formed contiguously with the overlap region 220 or they can be attached using surface or wall attachment means. One method for forming the inlet 215 and outlet 225 transition regions contiguously with the overlap region 220 is shown in FIGS. 11A–11E. FIG. 11A shows an inlet transition beveled attachment 520 that attaches the first 110 and fourth 145 quadrants together in the inlet transition region 215. The inlet transition beveled attachment 520 extends from the overlap inlet end first and fourth quadrant attachment 280 along a beveled angle to the outer surface zero degree line 65. Similarly, an outlet transition beveled attachment 525 is made extending from the overlap outlet end first and fourth quadrant attachment 285 along a beveled angle to the outer surface zero degree line 65. These inlet 520 and outlet 525 beveled attachments can be made using surface or wall attachment means as described earlier and can be a curved line attachment; beveled line attachments are not required to be a straight line.

An inlet transition beveled cut 530 is made through the first 110 and fourth 145 quadrants adjacent to the inlet transition beveled attachment 520 on the side of the attachment nearest to the outer surface zero degree line 65 as shown in FIG. 11C. Similarly, an outlet transition beveled cut 535 is made through the first 110 and fourth 145 quadrants adjacent to the outlet transition beveled attachment 520. The inlet 540 and outlet 545 transition excess tissue can be removed. The inlet 215 and outlet 225 transition regions provide a smooth contiguous transition from the overlap region 220 to the inlet 230 and outlet 235 distended vein as shown in FIG. 11E.

Figure 14A:
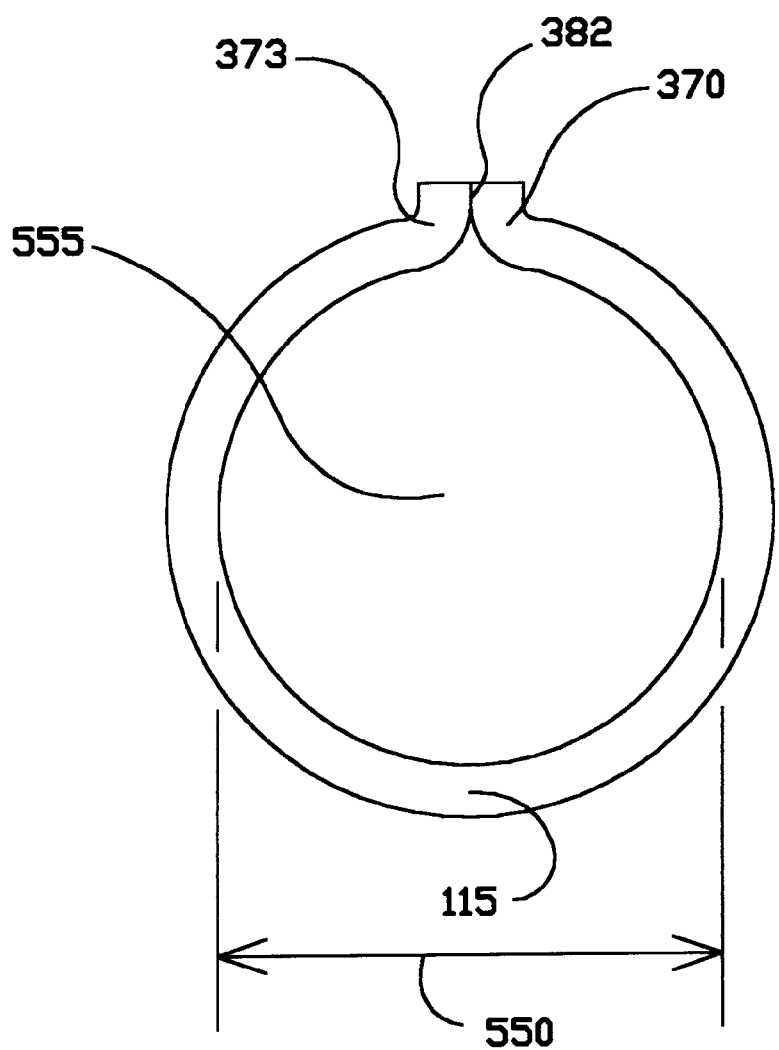
FIG. 14A is a sectional view of an alternate inlet transition region embodiment near the overlap region with antegrade blood flow.
Figure 14B:
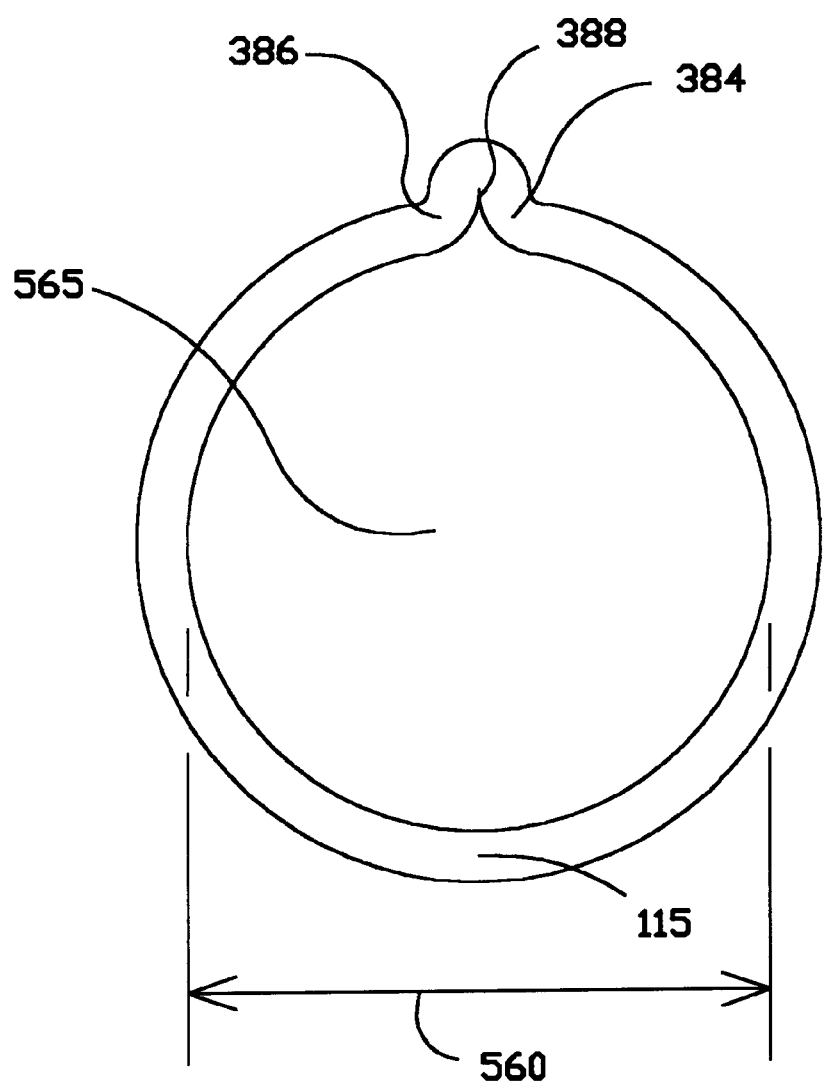
FIG. 14B is a sectional view of an alternate inlet transition region embodiment near the inlet distended vein with antegrade blood flow.

FIGS. 14A and 14B are sectional views of the inlet transition region 215. The 180 degree wall 115 is shown for reference. As shown in FIG. 14A approximately the 45 degree wall 370 can be attached to approximately the 315 degree wall 373 at an inlet transition 45 and 315 degree wall attachment 382. As shown in FIG. 14B approximately the 20 degree wall 384 can be attached to approximately the 340 degree wall 386 at the inlet transition 20 and 340 degree wall attachment 388. Additional inlet transition attachments are made in a manner to form the inlet transition beveled attachment 520 shown in FIG. 11A. An inlet transition diameter 550 for the inlet transition flow lumen 555 of FIG. 14A is smaller that an inlet transition diameter 560 for an inlet transition flow lumen 565 of FIG. 14B. The inlet transition excess tissue 540 (see FIG. 11C) that was attached to the first 110 or fourth 145 quadrant wall has been trimmed off and removed.

Figure 15A:
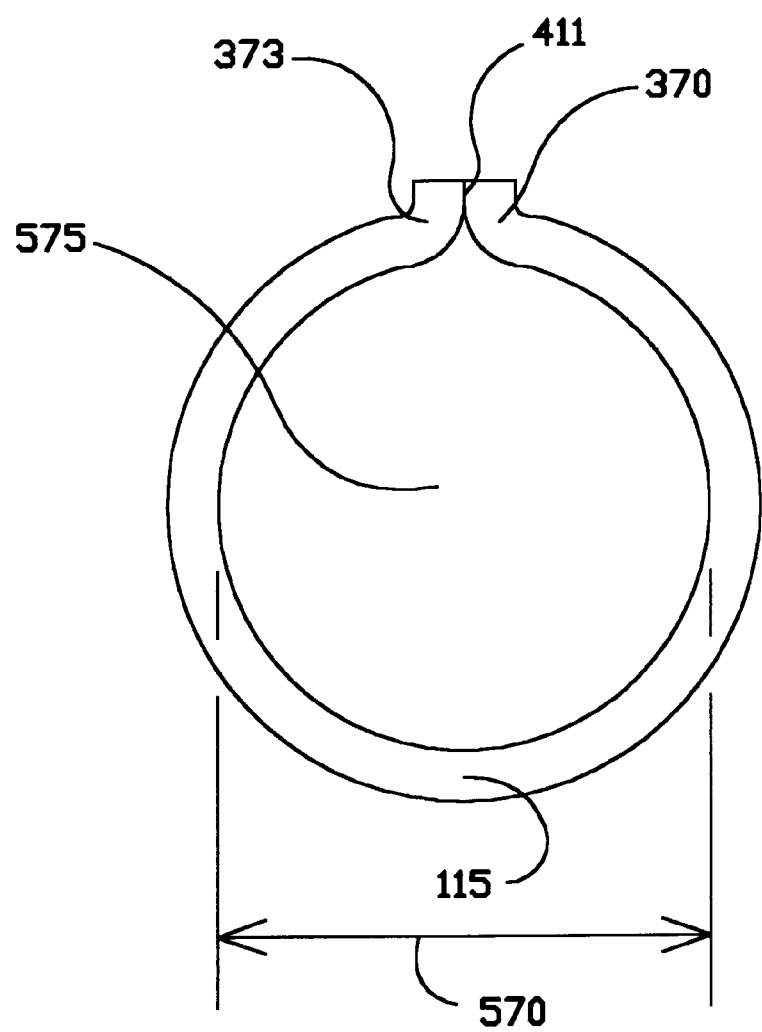
FIG. 15A is a sectional view of an alternate outlet transition region embodiment near the overlap region with antegrade blood flow.
Figure 15B:
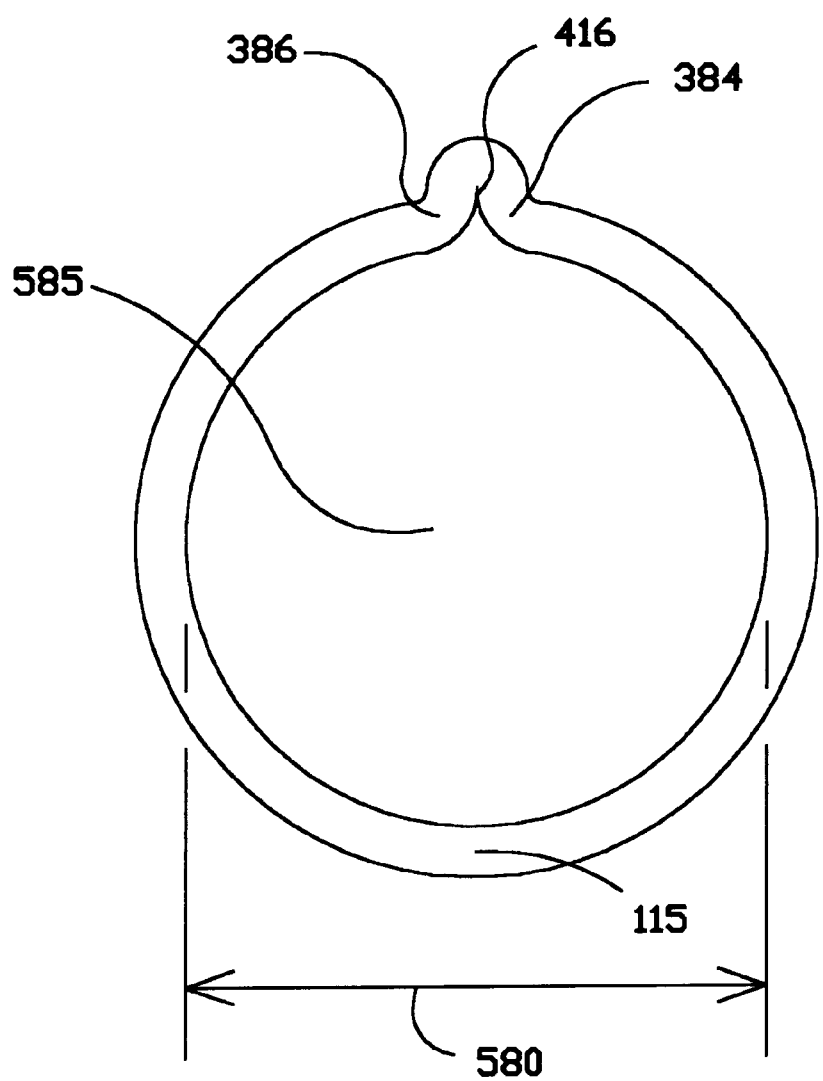
FIG. 15B is a sectional view of an alternate outlet transition region embodiment near the outlet distended vein with antegrade blood flow.

FIGS. 15A and 15B are sectional views of the outlet transition region 225. As shown in FIG. 15A approximately the 45 degree wall 370 can be attached to approximately the 315 degree wall 373 at an outlet transition 45 and 315 degree wall attachment 411. As shown in FIG. 15B approximately the 20 degree wall 384 can be attached to approximately the 340 degree wall 386 at the outlet transition 20 and 340 degree wall attachment 416. Additional outlet transition attachments are made in a manner to form the outlet transition beveled attachment 525 shown in FIG. 11A. An outlet transition diameter 570 for the outlet transition flow lumen 575 of FIG. 15A is smaller than an outlet transition diameter 580 for an outlet transition flow lumen 585 of FIG. 15B. The outlet transition excess tissue 545 (see FIG. 11C) that was attached to the first 110 or fourth 145 quadrant wall has been trimmed off and removed.

Figure 16:
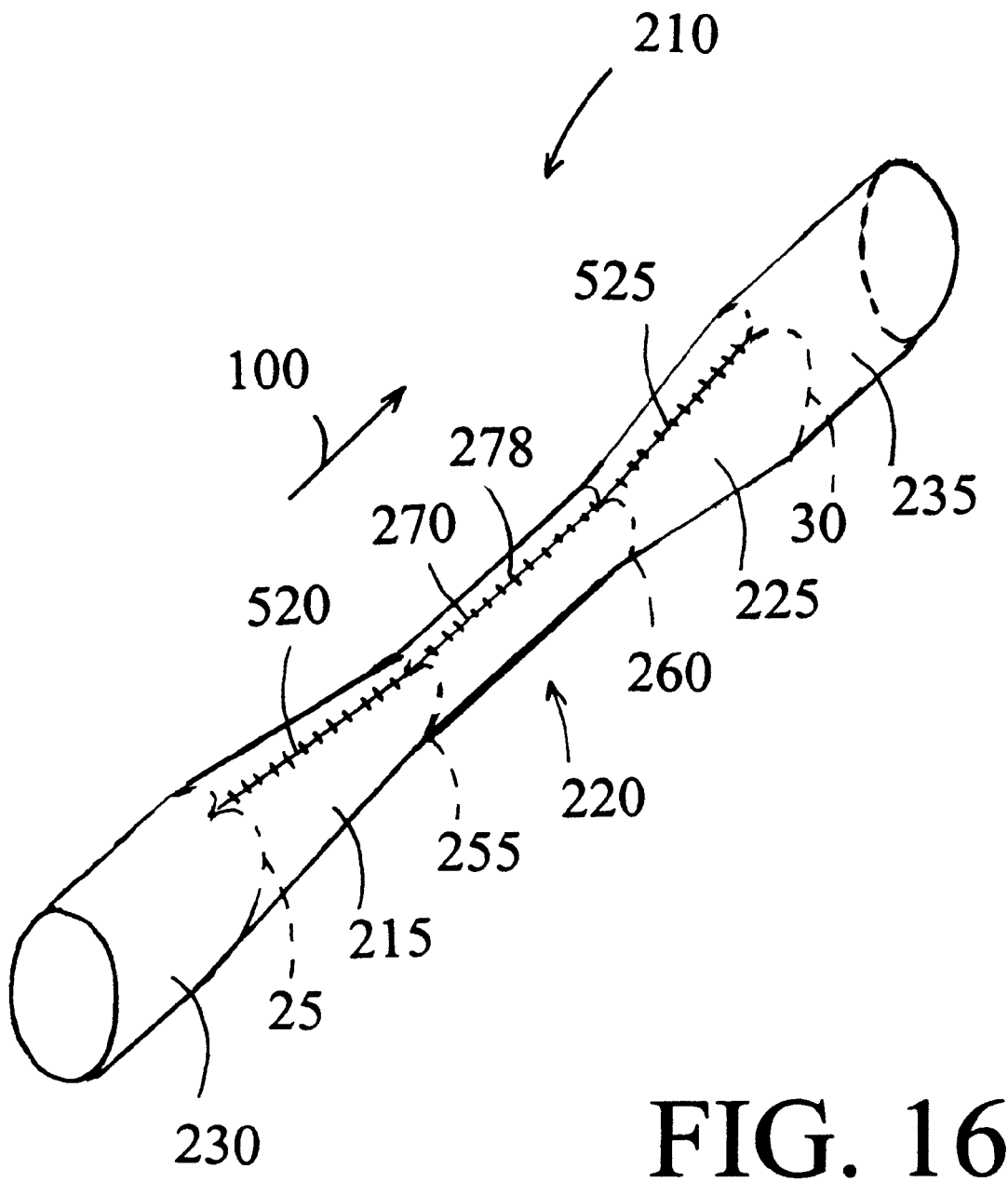
FIG. 16 is an isometric view of an alternate embodiment of the venous valve of this invention.

FIGS. 16 shows an isometric view of one embodiment of the venous valve 210 of the present invention. The overlap region 220 is contiguously joined to the inlet 215 and outlet 225 transition regions which are contiguously joined to the inlet 230 and outlet 235 distended veins, respectively. The inlet 215 and outlet 225 transition regions have inlet 520 and outlet 525 transition bevel attachments, respectively. The overlap region 220 has an outer surface 90 and 270 degree line attachment 270 extending from the overlap inlet end 255 to the overlap outlet end 260.

The inner and outer surface line attachments and wall attachments presented in this disclosure describe FIGS. 1–16 in a clear manner. It is understood that in forming the venous valve 210 of the present invention the attachments made from one quadrant or sector to another are not required to be the surface line or wall line attachments as they are presented in FIGS. 1–16 and their descriptions. A wall line attachment for example could occur over only a portion of the overlap region 220 and it is not required to extend parallel to the centerline 40; a surface or wall line attachment is only required to have a directional component in the direction of the centerline 40 or axial direction 60. Surface line attachments and wall line attachments can be beveled or formed at an angle with respect to the centerline 40. Wall line attachments made at the overlap inlet or outlet end can be beveled or formed at an angle with respect to the centerline 40. A portion of a wall area 21 from one quadrant or sector can be attached to the wall area 21 of another quadrant or sector; this surface or wall attachment can be used to form a portion of the valve cusp or form the attachments found on other aspects of the venous valve described in this disclosure.

It is understood that the overlap region of one embodiment can be combined with an inlet or outlet transition region of another embodiment. The method of forming the venous valve of this invention can also involve combinations describing the formation of the overlap region or transition region from any of the embodiments presented in this disclosure. Furthermore, it is understood that the valve of this invention can be formed from a combination of autologous tissue used for either the overlap region or a transition region combined with heterogeneous biological tissue or synthetic material used for another portion of the venous valve.

Various modifications can be made to a present invention without departing from the apparent scope hereof.

We claim:

1. A venous valve for directing antegrade blood flow in an autologous vein of the body that requires a venous valve, said venous valve comprising a tubular conduit means from which said venous valve is formed, said tubular conduit means having a tubular conduit inlet end, a tubular conduit outlet end, and a tubular conduit wall;
   a portion of the tubular conduit wall being attached to another portion of the tubular conduit wall substantially from the inlet to the outlet end of said tubular conduit means forming two tubular members, a first tubular member having a first tubular member wall, and a second tubular member having a second tubular member wall;
   a portion of said first tubular member wall being attached to a portion of said second tubular member wall to position a substantial portion of said first tubular member wall in approximation with a substantial portion of said second tubular member wall with an approximation attachment;
   an inlet end of said second tubular member having a closure attachment to prevent antegrade blood flow from entering said second tubular member and to prevent retrograde blood flow from passing through said second tubular means;
   a portion of said first tubular member wall being attached via a valve cusp attachment to a portion of said second tubular member wall at approximately the outlet end of said tubular conduit member to form at least a portion of a valve cusp, said valve cusp directing retrograde blood flow into an outlet end of said second tubular member and preventing substantial retrograde blood flow through said first tubular member;
   whereby said venous valve directs antegrade blood flow from said tubular conduit inlet end to said tubular conduit outlet end and prevents substantial retrograde blood flow from said tubular conduit outlet end to said tubular conduit inlet end.

2. The venous valve of claim 1 wherein said tubular conduit means is an autologous vein segment with endothelium on at least a portion of an inner surface.

3. The venous valve of claim 2 wherein said autologous vein segment is contiguous with the autologous vein that requires a venous valve.

4. The venous valve of claim 2 wherein said valve cusp has an endothelialized surface.

5. The venous valve of claim 2 wherein said valve cusp has an inverted fold with endothelium covering said valve cusp.

6. The venous valve of claim 1 further comprising an inlet transition region joined to said tubular conduit means and extending from said tubular conduit inlet end to an inlet end of the autologous vein requiring a venous valve, said inlet transition region having a tapered tubular shape with an inlet transition lumen.

7. The venous valve of claim 6 wherein said inlet transition region has an inlet transition beveled attachment formed by the attachment of a portion of a first sector to a portion of a second sector along a wall line that extends from said tubular conduit inlet end to the inlet end of the autologous vein requiring a venous valve.

8. The venous valve of claim 7 wherein excess inlet transition tissue extends outside said inlet transition beveled attachment and outside said inlet transition lumen.

9. The venous valve of claim 8 wherein said excess inlet transition tissue is cut off or removed.

10. The venous valve of claim 7 wherein excess inlet transition tissue extends inside said inlet transition beveled attachment and inside said inlet transition lumen.

11. The venous valve of claim 1 further comprising an outlet transition region joined to said tubular conduit means extending from said tubular conduit outlet end to an outlet end of the autologous vein requiring a venous valve, said outlet transition region having a tapered tubular shape with an outlet transition lumen.

12. The venous valve of claim 11 wherein said outlet transition region has an outlet transition beveled attachment formed by the attachment of a portion of a first sector to a portion of a second sector along a wall line that extends from said tubular conduit outlet end to the outlet end of the autologous vein requiring a venous valve.

13. The venous valve of claim 12 wherein excess outlet transition tissue extends inside said outlet transition attachment and inside said outlet transition lumen.

14. The venous valve of claim 1 further comprising;
   A. an inlet transition region joined to said tubular conduit means extending from said tubular conduit inlet end to an inlet end of the autologous vein requiring a venous valve, said inlet transition region having a tapered tubular shape with an inlet transition lumen, and;
   B. an outlet transition region joined to said tubular conduit means extending from said tubular conduit outlet end to an outlet end of the autologous vein requiring a venous valve, said outlet transition region having a tapered tubular shape with an outlet transition lumen.

15. The venous valve of claim 14 wherein said inlet and outlet transition regions are formed from an autologous vein segment.

16. The venous valve of claim 15 wherein said autologous vein segment is contiguous with the autologous vein that requires a venous valve.

17. The venous valve of claim 1 wherein said valve cusp has a valve cusp length in a generally axial direction that is greater than one half of a diameter of said first tubular member.

18. The venous valve of claim 1 wherein said first tubular member has a first tubular member diameter that is less than the diameter of the autologous vein that requires a venous valve.

19. The venous valve of claim 1 wherein said approximation attachment, said closure attachment, and said valve cusp attachment is comprised of attachment means taken from a group consisting of staples, suture, adhesives, bonding agents, metal strand material, polymeric strand material, laser fusion, or thermal fusion.

20. The venous valve of claim 1 wherein said tubular conduit means has a wall support means attached to prevent distension of at least a portion of said tubular conduit means.

21. The venous valve of claim 1 wherein said first tubular member or said second tubular member have wall support means attached to said first tubular member wall or said second tubular member wall between said inlet and outlet end of said first or second tubular member to prevent distension.

22. The venous valve of claim 1 wherein said tubular conduit means is a nonautologous biological conduit.

23. The venous valve of claim 1 wherein said tubular conduit means is an autologous tissue formed into a tubular shape.

24. The venous valve of claim 1 wherein said tubular conduit means is a polymeric conduit.

25. The venous valve of claim 1 wherein said tubular conduit means is a conduit formed of a composite material.

26. A venous valve for directing antegrade blood flow in a vascular conduit of a body that requires a venous valve, said venous valve comprising a tubular conduit means from which said venous valve is formed, said tubular conduit means having a tubular conduit inlet end, a tubular conduit outlet end, and a tubular conduit wall, said tubular conduit wall having tubular conduit wall lines that extend within said tubular conduit wall and having a tubular conduit axial direction component, said tubular conduit wall being divided into sectors;
- at least a portion of a wall line of one sector forming a divisional attachment to at least a portion of a wall line of another sector to form two tubular members, a first tubular member having a first tubular member wall, and first tubular member wall lines within said first tubular member wall with an axial direction component, and a second tubular member having a second tubular member wall and second tubular member wall lines within said second tubular member wall with an axial direction component;
- at least a portion of at least one of said first tubular member wall lines forms an approximation attachment to at least a portion of at least one of said second tubular member wall lines to position at least a portion of said first tubular member wall in approximation with at least a portion of said second tubular member wall;
- at least a portion of said second tubular member wall at an inlet end of said second tubular member forms a closure attachment to prevent antegrade blood flow from entering said second tubular member and to prevent retrograde blood flow from passing through said second tubular member;
- a portion of said first tubular member wall forms a valve cusp attachment to a portion of said second tubular member wall to form at least a portion of a valve cusp, said valve cusp directing retrograde blood flow into said second tubular member and preventing retrograde blood flow through said first tubular member;
- whereby said venous valve directs antegrade blood flow from said tubular conduit inlet end to said tubular conduit outlet end and prevents retrograde blood flow from said tubular conduit outlet end to said tubular conduit inlet end.

27. A venous valve for directing antegrade blood flow in a vascular conduit of a body that requires a venous valve, said venous valve comprising a tubular means from which said venous valve is formed, said tubular means having a tubular conduit inlet end, a tubular conduit outlet end, and a tubular conduit wall, said tubular conduit wall having tubular conduit wall lines that extend within said tubular conduit wall and having a tubular conduit axial direction component;
- a portion of one wall line being attached to a portion of another wall line forming two tubular members, a first tubular member having a first tubular member wall, and first tubular member wall lines with an axial direction component, and a second tubular member having a second tubular member wall and second tubular member wall lines with an axial direction component;
- a portion of at least one of said first tubular member wall lines being attached to a portion of at least one of said second tubular member wall lines to position a portion of said first tubular member wall in approximation with a portion of said second tubular member wall;
- a portion of said second tubular member wall at a first end of said second tubular member being attached to prevent antegrade blood flow from entering said first end of said second tubular member and to prevent retrograde blood flow from passing through said second tubular member;
- a portion of said first tubular member wall being attached to a portion of said second tubular member wall to form at least a portion of a valve cusp, said valve cusp directing retrograde blood flow into a second end of said second tubular member and preventing retrograde blood flow through said first tubular member;
- whereby said venous valve directs antegrade blood flow from said tubular conduit inlet end to said tubular conduit outlet end and prevents retrograde blood flow from said tubular conduit outlet end to said tubular conduit inlet end.

28. A venous valve for directing antegrade venous blood flow in the vascular system of a body toward the heart through an autologous vein with that requires a venous valve, said venous valve comprising;
- A. a tubular conduit means from which said venous valve is formed, said tubular conduit means having a tubular conduit inlet end, a tubular conduit outlet end, a tubular conduit axial direction, a tubular conduit axial length, a tubular conduit diameter, and a tubular conduit wall, said tubular conduit wall having tubular conduit wall lines that extend within said tubular conduit wall and having a tubular conduit axial direction component, said tubular conduit wall being divided into sectors, said tubular conduit wall having an inner surface and an outer surface;
- B. a divisional attachment formed by the attachment of at least a portion of a first sector wall line of a first sector to at least a portion of a second sector wall line of a second sector along at least a portion of the axial length of said tubular means to form two tubular members of said tubular means, a first tubular member and a second tubular member, said first tubular member having a first tubular member inlet end, first tubular member outlet end, first tubular member wall, and first tubular member wall lines within said first tubular member wall with a first tubular member axial direction component, and said second tubular member having a second tubular member inlet end, second tubular member outlet end, second tubular member wall, and second tubular member wall lines within said second tubular member wall with a second tubular member axial direction component;

C. an approximation attachment formed by the attachment of at least a portion of at least one of said first tubular member wall lines to at least a portion of at least one of said second tubular member wall lines to position at least a portion of said first tubular member wall in approximation with at least a portion of said second tubular member wall;

D. a closure attachment formed by the attachment of at least a portion of said second tubular member wall at said second tubular member inlet end to substantially prevent antegrade blood flow from entering said second tubular member inlet end and to substantially prevent retrograde flow from flowing through said second tubular member;

E. a valve cusp attachment formed by the attachment of a portion of said first tubular member wall to a portion of said second tubular member wall to form at least a portion of a valve cusp, said valve cusp substantially preventing retrograde blood flow through said first tubular member.

29. A method for forming a venous valve for directing antegrade venous blood flow through a vein, said method comprising the steps of;

A. identifying and isolating a tubular conduit means from which said venous valve is formed, said tubular conduit means having a tubular conduit inlet end, a tubular conduit outlet end, and a tubular conduit wall;

B. forming a divisional attachment between two portions of tubular conduit means to form two tubular members, a first and second tubular member, with first and second tubular member walls, respectively;

C. forming a closure attachment at an inlet end of said second tubular member to prevent antegrade blood flow from entering said second tubular member and to substantially prevent retrograde flow from flowing through said second tubular member;

D. forming a valve cusp attachment by attaching a portion of wall of said first tubular member wall to a portion of wall of said second tubular member wall using attachment means to form at least a portion of a valve cusp; said valve cusp directing retrograde blood flow into an outlet end of said second tubular member and substantially preventing retrograde blood flow through said first tubular member;

E. forming an approximation attachment by attaching at least a portion of said first tubular member wall to at least a portion of said second tubular member wall using attachment means to position at least a portion of said first tubular member wall in approximation with at least a portion of said second tubular member wall;

F. thereby directing antegrade blood flow through said first tubular member and substantially preventing retrograde blood flow through said first tubular member.

30. The method of claim 29 wherein said venous valve is formed with the tubular conduit means in substantially a flat conformation.

31. The method of claim 29 wherein said attachment means are selected from the group consisting of suture, staples, metallic fiber, polymeric fiber, adhesives, biological bonding agents, laser fusion methods, and thermal fusion methods.

32. The method of claim 29 wherein said tubular conduit means is an autologous vein segment with an inlet end and an outlet end, said autologous vein segment being contiguous with an autologous vein requiring a venous valve and the formation of said venous valve being conducted in situ.

33. The method of claim 32 further comprising the steps of;

A. forming an inlet transition region from said autologous vein segment, said inlet transition region having a tapered tubular shape with an inlet transition lumen and extending from said tubular conduit inlet end to said autologous vein requiring a venous valve;

B. forming an outlet transition region from said autologous vein segment, said outlet transition region having a tapered tubular shape with an outlet transition lumen and extending from said tubular conduit outlet end to said autologous vein requiring a venous valve.

34. The method of claim 32 wherein said forming of said valve cusp attachment comprises the steps of;

A. forming a transverse attachment along a portion of said inlet end and said outlet end of said autologous vein segment;

B. cutting said autologous vein segment adjacent to said inlet and outlet end;

C. forming an inverted fold between said inlet and outlet end of said autologous vein segment, thereby providing a valve cusp that is entirely endothelialized.

35. The method of claim 33 further comprising the steps;

A. forming an inlet transition beveled attachment by attaching a portion of a first sector to a portion of a second sector along a wall line that extends from said tubular conduit inlet end to the autologous vein requiring a venous valve;

B. forming excess tissue outside said inlet transition attachment and outside said inlet transition lumen.

36. The method of claim 35 further comprising the steps of cutting off and removing said excess tissue using scissors, scalpel, or other cutting means.

37. The method of claim 33 further comprising the steps;

A. forming an inlet transition beveled attachment by attaching a portion of a first sector to a portion of a second sector along a wall line that extends from said first tubular member inlet end and said second tubular member inlet end to the autologous vein requiring a venous valve;

B. forming an outlet transition attachment by attaching a portion of a first sector to a portion of a second sector along a wall line that extends from said first tubular member outlet end and said second tubular member outlet end to the autologous vein requiring a venous valve;

C. forming excess tissue outside said inlet and said outlet transition attachment and outside said inlet and outlet transition lumen.

38. The method of claim 33 further comprising the steps;

A. forming an inlet transition beveled attachment by attaching a portion of a first sector to a portion of a second sector along a wall line that extends from said first tubular member inlet end and said second tubular member inlet end to the autologous vein requiring a venous valve;

B. forming an outlet transition beveled attachment by attaching a portion of a first sector to a portion of a second sector along a wall line that extends from said first tubular member outlet end and said second tubular member outlet end to the autologous vein requiring a venous valve;

C. forming excess tissue inside said inlet and said outlet transition attachment and inside said inlet and outlet transition lumen.

39. The method of claim 29 wherein said tubular conduit means is not an autologous vein segment contiguous with an autologous vein requiring a venous valve, said tubular conduit means being formed into said venous valve and implanted interpositionally into the autologous vein that requires a venous valve using attachment means to provide a leak free seal between said venous valve and said autologous vein requiring a venous valve.

40. A method for forming a venous valve for directing antegrade venous blood flow through a vein, said method comprising the steps of;
  A. identifying and providing a tubular conduit means from which said venous valve is formed, said tubular conduit means having a tubular conduit inlet end, a tubular conduit outlet end, and a tubular conduit wall, said tubular conduit wall having tubular conduit wall lines that extend within said tubular conduit wall and having a tubular conduit axial direction component, said tubular conduit wall being divided into sectors;
  B. forming an inlet valve cusp attachment by attaching a portion of a tubular conduit wall from a first sector to a tubular conduit wall of a second sector at approximately the inlet end of said tubular conduit means to form at least a portion of a valve cusp;
  C. forming an outlet valve cusp attachment by attaching a portion of a tubular conduit wall from a first sector to a tubular conduit wall of a second sector at approximately the outlet end of said tubular conduit means to form at least a portion of a valve cusp;
  D. cutting said tubular conduit means adjacent to and in a retrograde direction from said inlet valve cusp attachment, and cutting said tubular conduit means adjacent to an in an antegrade direction from said outlet valve cusp attachment;
  E. invert folding the first and second sectors such that a first wall line located adjacent to said first and second sectors is in apposition to a second wall line that is not adjacent to said first and second sectors;
  F. forming a divisional attachment by attaching at least a portion of said first wall line to at least a portion of said second wall line to form two tubular members, a first tubular member having a first tubular member wall and providing an antegrade blood through-flow path, and a second tubular member having a second tubular member wall and providing at least a portion of a sinus member;
  G. forming a closure attachment by attaching said second tubular member wall at approximately the inlet end of said tubular conduit means using attachment means to prevent antegrade blood flow from entering said second tubular member inlet end and to prevent retrograde blood flow from passing through said second tubular member;
  H. forming an approximation attachment by attaching at least a portion of said first tubular member wall to at least a portion of said second tubular member wall using attachment means to position at least a portion of said first tubular member wall in approximation with at least a portion of said second tubular member wall thereby causing said valve cusp to prevent retrograde blood flow through said first tubular member and allow antegrade blood flow through said first tubular member.

41. The method of claim 40 wherein said tubular conduit means is an autologous vein segment with an inlet end and an outlet end, said autologous vein segment being contiguous with an autologous vein requiring a venous valve and the formation of said venous valve is in situ.

42. The method of claim 41 further comprising the steps of;
  A. forming an inlet transition region from said autologous vein segment, said inlet transition region having a tapered tubular shape with an inlet transition lumen and extending from said tubular conduit inlet end to said autologous vein requiring a venous valve;
  B. forming an outlet transition region from said autologous vein segment, said outlet transition region having a tapered tubular shape with an outlet transition lumen and extending from said tubular conduit outlet end to said autologous vein requiring a venous valve.

* * * * *